United States Patent [19]

Wollenberg et al.

[11] Patent Number: 4,840,744

[45] Date of Patent: Jun. 20, 1989

[54] MODIFIED SUCCINIMIDES AND LUBRICATING OIL COMPOSITIONS CONTAINING THE SAME

[75] Inventors: Robert H. Wollenberg, San Rafael; Frank Plavac, Novato; Timothy R. Erdman, San Rafael, all of Calif.

[73] Assignee: Chevron Research Company, San Francisco, Calif.

[21] Appl. No.: 186,512

[22] Filed: Apr. 26, 1988

Related U.S. Application Data

[60] Division of Ser. No. 90,187, Aug. 27, 1987, Pat. No. 4,746,446, which is a division of Ser. No. 864,166, May 16, 1986, which is a division of Ser. No. 722,939, Apr. 12, 1985, Pat. No. 4,612,132, which is a continuation-in-part of Ser. No. 632,777, Jul. 20, 1984, abandoned.

[51] Int. Cl.$^4$ .......................................... C10M 133/44
[52] U.S. Cl. .......................... 252/51.5 A; 252/51.5 R
[58] Field of Search .................... 252/51.5 A, 51.5 R; 548/545, 546; 549/228, 230

[56] References Cited

U.S. PATENT DOCUMENTS

| | | | |
|---|---|---|---|
| 2,802,022 | 8/1957 | Groszos et al. | 260/471 |
| 2,844,451 | 7/1958 | Alpert et al. | 44/70 |
| 2,991,162 | 7/1961 | Malec | 44/58 |
| 3,216,936 | 11/1965 | Le Suer | 252/51.5 |
| 3,367,943 | 2/1968 | Miller et al. | 260/326.3 |
| 3,373,111 | 3/1968 | Le Suer et al. | 252/51.5 |
| 3,652,240 | 3/1972 | Dorn et al. | 44/66 |
| 3,862,981 | 1/1975 | Demoures et al. | 252/51.5 |
| 4,460,381 | 7/1984 | Karol et al. | 44/63 |
| 4,482,464 | 11/1984 | Karol et al. | 252/51.5 A |
| 4,490,154 | 12/1984 | Sung et al. | 44/70 |
| 4,501,597 | 2/1985 | Karol et al. | 44/63 |
| 4,584,117 | 4/1986 | Wollenberg | 252/51.5 A |
| 4,617,137 | 10/1986 | Plavac | 252/49.6 |
| 4,645,515 | 2/1987 | Wollenberg | 44/63 |
| 4,648,886 | 3/1987 | Buckley, III et al. | 44/63 |
| 4,664,827 | 5/1987 | Buckley | 252/49.6 |
| 4,695,391 | 9/1987 | Buckley | 252/51.5 R |
| 4,746,446 | 5/1988 | Wollenberg et al. | 252/51.5 A |
| 4,746,447 | 5/1988 | Wollenberg | 252/51.5 A |
| 4,747,963 | 5/1988 | Wollenberg | 252/51.5 A |

FOREIGN PATENT DOCUMENTS

90629 10/1983 European Pat. Off.
689705 4/1953 United Kingdom .

*Primary Examiner*—Jacqueline V. Howard
*Attorney, Agent, or Firm*—S. R. Paglia; R. C. Gaffney; J. J. DeYoung

[57] ABSTRACT

Disclosed are additives which are useful as dispersants in lubricating oils, gasolines, marine crankcase oils and hydraulic oils. In particular, disclosed are polyamino alkenyl or alkyl succinimides which contain carbamate functionalities.

43 Claims, No Drawings
}

MODIFIED SUCCINIMIDES AND LUBRICATING OIL COMPOSITIONS CONTAINING THE SAME

CROSS-REFERENCE TO RELATED APPLICATIONS

This application is a division of pending application Ser. No. 090,187, filed Aug. 27, 1987 now U.S. Pat. No. 4,746,446, which in turn is a division of pending application Ser. No. 864,166, filed May 16, 1986, which in turn is a division of application Ser. No. 722,939, filed Apr. 12, 1985 now U.S. Pat. No. 4,612,132, which in turn is a continuation-in-part of application Ser. No. 632,777, filed July 20, 1984, which is now abandoned.

BACKGROUND OF THE INVENTION

1. Field of the Invention

This invention relates to additives which are useful as dispersants and/or detergents in lubricating oils. In particular, this invention is directed toward polyamino alkenyl or alkyl succinimides wherein one or more of the amino nitrogens of the succinimide has been converted to a hydrocarbyl carbamate, a hydroxyhydrocarbylcarbamate or a hydroxy polyoxyalkylene carbamate. The modified polyamino alkenyl or alkyl succinimides of this invention have been found to possess improved dispersancy and/or detergency properties when employed in a lubricating oil. These modified succinimides are also useful as detergents and/or dispersants in fuels.

2. Prior Art

Alkenyl or alkyl succinimides have been previously modified with alkylene oxides to produce poly(oxyalkylene)hydroxy derivatives thereof. These alkylene oxide treated succinimides are taught as additives for lubricating oils (see U.S. Pat. Nos. 3,373,111 and 3,367,943). U S. Pat. No. 2,991,162 discloses carburetor detergent additives for gasoline obtained by reacting an N-alkyl propylene diamine with ethylene carbonate to produce a two-component detergent additive consisting of a carbamate and a urea compound. U.S. Pat. No. 3,652,240 discloses carburetor detergent additives for hydrocarbonaceous fuel which are carbamates formed by the reaction of an amino-amide with ethylene carbonate. Karol et al, U.S. Pat No. 4,460,381 discloses oxalic acid derivatives of mono- or bissuccinimides as fuel stabilizers. Karol et al, U.S. Pat. No. 4,482,464, discloses succinimides which have been modified by treatment with a hydroxyalkylene carboxylic acid selected from glycolic acid, lactic acid, 2-hydroxymethyl propionic acid and 2,2'-bis-hydroxymethylpropionic acid. These modified succinimides of U.S. Pat. No. 4,482,464 are disclosed as lubricating oil additives. U.S. Pat. No. 4,490,154 discloses fuels containing an alkenylsuccinyl polyglycolcarbonate ester as a deposit control additive. U.S. Pat. No. 3,216,936 discloses a product prepared from an aliphatic amine, a polymer substituted succinic acid and an aliphatic monocarboxylic acid. However, there is no teaching in these patents, or apparently elsewhere, to modify these polyamino alkenyl or alkyl succinimides in the manner of this invention.

SUMMARY OF THE INVENTION

It has now been found that polyamino alkenyl or alkyl succinimides may be modified to yield a polyamino alkenyl or alkyl succinimide wherein one or more of the nitrogens of the polyamino moiety is substituted with a hydrocarbyl oxycarbonyl, a hydroxyhydrocarbyl oxycarbonyl or a hydroxy poly(oxyalkylene) oxycarbonyl. These modified succinimides are improved dispersants and/or detergents for use in fuels or oils. Accordingly, the present invention also relates to a lubricating oil composition comprising a major amount of an oil of lubricating viscosity and an amount of a modified polyamino alkenyl or alkyl succinimide sufficient to provide dispersancy and/or detergency.

Another composition aspect of this invention is a fuel composition comprising a major portion of a hydrocarbon boiling in a gasoline or diesel range and an amount of a modified polyamino alkenyl or alkyl succinimide sufficient to provide dispersancy and/or detergency.

DETAILED DESCRIPTION OF THE INVENTION

The modified polyamino alkenyl or alkyl succinimides of this invention are prepared from a polyamino alkenyl or alkyl succinimide. In turn, these materials are prepared by reacting an alkenyl or alkyl succinic anhydride with a polyamine as shown in reaction (1) below:

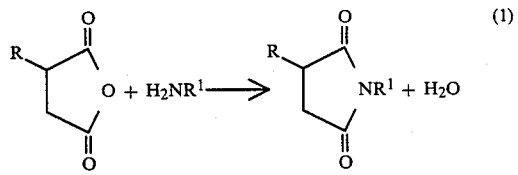

wherein R is an alkenyl or alkyl group of from 10 to 300 carbon atoms; and $R^1$ is the remainder of the polyamino moiety.

In general, the alkenyl or alkyl group of the succinimide is from 10 to 300 carbon atoms. While the modified succinimides of this invention possess good detergency properties even for alkenyl or alkyl groups of less than 20 carbon atoms, dispersancy is enhanced when the alkenyl or alkyl group is at least 20 carbon atoms. Accordingly, in a preferred embodiment, the alkenyl or alkyl group of the succinimide is at least 20 carbon atoms.

These alkenyl or alkyl succinimides that can be used herein are disclosed in numerous references and are well known in the art. Certain fundamental types of succinimides and related materials encompassed by the term of art "succinimide" are taught in U.S. Pat. Nos. 2,992,708; 3,018,291; 3,024,237; 3,100,673; 3,219,666; 3,172,892; and 3,272,746, the disclosures of which are hereby incorporated by reference. The term "succinimide" is understood in the art to include many of the amide, imide and amidine species which are also formed by this reaction. The predominant product however is succinimide and this term has been generally accepted as meaning the product of a reaction of an alkenyl substituted succinic acid or anhydride with a polyamine as shown in reaction (1) above. As used herein, included within this term are the alkenyl or alkyl mono-, bis-succinimides and other higher analogs.

A(1) Succinic Anhydride

The preparation of the alkenyl-substituted succinic anhydride by reaction with a polyolefin and maleic anhydride has been described, e.g., U.S. Pat. Nos. 3,018,250 and 3,024,195 Such methods include the thermal reaction of the polyolefin with maleic anhydride and the reaction of a halogenated polyolefin, such as a chlorinated polyolefin, with maleic anhydride. Reduction of the alkenyl-substituted succinic anhydride yields the corresponding alkyl derivative. Alternatively, the alkenyl substituted succinic anhydride may be prepared as described in U.S. Pat. Nos. 4,388,471 and 4,450,281 which are totally incorporated herein by reference.

Polyolefin polymers for reaction with the maleic anhydride are polymers comprising a major amount of $C_2$ to $C_5$ mono-olefin, e.g., ethylene, propylene, butylene, isobutylene and pentene. The polymers can be homopolymers such as polyisobutylene as well as copolymers of 2 or more such olefins such as copolymers of: ethylene and propylene, butylene, and isobutylene, etc. Other copolymers include those in which a minor amount of the copolymer monomers, e.g., 1 to 20 mole percent is a $C_4$ to $C_8$ nonconjugated diolefin, e.g., a copolymer of isobutylene and butadiene or a copolymer of ethylene, propylene and 1,4-hexadiene, etc.

The polyolefin polymer, the alkenyl or alkyl moiety which is represented as R, usually contains from about 10 to 300 carbon atoms, although preferably 10 to 200 carbon atoms; more preferably 12 to 100 carbon atoms and most preferably 20–100 carbon atoms.

A particularly preferred class of olefin polymers comprises the polybutenes, which are prepared by polymerization of one or more of 1-butene, 2-butene and isobutene. Especially desirable are polybutenes containing a substantial proportion of units derived from isobutene. The polybutene may contain minor amounts of butadiene which may or may not be incorporated in the polymer. Most often the isobutene units constitute 80%, preferably at least 90%, of the units in the polymer. These polybutenes are readily available commercial materials well known to those skilled in the art. Disclosures thereof will be found, for example, in U.S. Pat. Nos. 3,215,707; 3,231,587; 3,515,669; and 3,579,450, as well as U.S. Pat. No. 3,912,764. The above are incorporated by reference for their disclosures of suitable polybutenes.

In addition to the reaction of a polyolefin with maleic anhydride, many other alkylating hydrocarbons may likewise be used with maleic anhydride to produce alkenyl succinic anhydride. Other suitable alkylating hydrocarbons include cyclic, linear, branched and internal or alpha olefins with molecular weights in the range 100–4,500 or more with molecular weights in the range of 200–2,000 being more preferred For example, alpha olefins obtained from the thermal cracking of paraffin wax. Generally, these olefins range from 5–20 carbon atoms in length. Another source of alpha olefins is the ethylene growth process which gives even number carbon olefins. Another source of olefins is by the dimerization of alpha olefins over an appropriate catalyst such as the well known Ziegler catalyst. Internal olefins are easily obtained by the isomerization of alpha olefins over a suitable catalyst such as silica.

A(2) Polyamine

The polyamine employed to prepare the polyamino alkenyl or alkyl succinimides is preferably a polyamine having from 2 to about 12 amine nitrogen atoms and from 2 to about 40 carbon atoms. The polyamine is reacted with an alkenyl or alkyl succinic anhydride to produce the polyamino alkenyl or alkyl succinimide, employed in this invention. The polyamine is so selected so as to provide at least one basic amine per succinimide. Since the reaction of a nitrogen of a polyamino alkenyl or alkyl succinimide to form a hydrocarbyl oxycarbonyl, a hydroxy hydrocarbyl oxycarbonyl or a hydroxy polyoxyalkylene oxycarbonyl is believed to efficiently proceed through a secondary or primary amine, at least one of the basic amine atoms of the polyamino alkenyl or alkyl succinimide must either be a primary amine or a secondary amine. Accordingly, in those instances in which the succinimide contains only one basic amine, that amine must either be a primary amine or a secondary amine. The polyamine preferably has a carbon-to-nitrogen ratio of from about 1:1 to about 10:1.

The polyamine portion of the polyamino alkenyl or alkyl succinimide may be substituted with substituents selected from (A) hydrogen, (B) hydrocarbyl groups of from 1 to about 10 carbon atoms, (C) acyl groups of from 2 to about 10 carbon atoms, and (D) monoketo, monohydroxy, mononitro, monocyano, lower alkyl and lower alkoxy derivatives of (B) and (C). "Lower", as used in terms like lower alkyl or lower alkoxy, means a group containing from 1 to about 6 carbon atoms. At least one of the substituents on one of the amines of the polyamine is hydrogen, e.g., at least one of the basic nitrogen atoms of the polyamine is a primary or secondary amino nitrogen atom.

Hydrocarbyl, as used in describing the polyamine components of this invention, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylenic and acetylenic, particularly acetylenic unsaturation. The substituted polyamines of the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxypropyl, hydroxyisopropyl, 4-hydroxybutyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, 2-(2-ethoxyethoxy)ethyl, 2-(2-(2-ethoxyethoxy)ethoxy)ethyl, 3,6,9,12-tetraoxatetradecyl, 2-(2-ethoxyethoxy)hexyl, etc. The acyl groups of the aforementioned (C) substituents are such as propionyl, acetyl, etc. The more preferred substituents are hydrogen, $C_1$–$C_6$ alkyls and $C_1$–$C_6$ hydroxyalkyls.

In a substituted polyamine the substituents are found at any atom capable of receiving them. The substituted atoms, e.g., substituted nitrogen atoms, are generally geometrically inequivalent, and consequently the substituted amines finding use in the present invention can be mixtures of mono- and polysubstituted polyamines with substituent groups situated at equivalent and/or inequivalent atoms.

The more preferred polyamine finding use within the scope of the present invention is a polyalkylene polyamine, including alkylene diamine, and including substituted polyamines, e.g., alkyl substituted polyalkylene polyamine. Preferably, the alkylene group contains from 2 to 6 carbon atoms, there being preferably from 2 to 3 carbon atoms between the nitrogen atoms. Such groups are exemplified by ethylene, 1,2-propylene, 2,2-dimethylpropylene, trimethylene, etc. Examples of such polyamines include ethylene diamine, diethylene triamine, di(trimethylene)triamine, dipropylene triamine, triethylene tetramine, tripropylene tetramine, tetraethylene pentamine, and pentaethylene hexamine. Such amines encompass isomers such as branched-chain polyamines and the previously mentioned substituted polyamines, including hydrocarbyl-substituted polyamines. Among the polyalkylene polyamines, those containing 2-12 amine nitrogen atoms and 2-24 carbon atoms are especially preferred, and the $C_2$–$C_5$ alkylene polyamines are most preferred, in particular, the lower polyalkylene polyamines, e.g., ethylene diamine, dipropylene triamine, etc.

The polyamine component also may contain heterocyclic polyamines, heterocyclic substituted amines and substituted heterocyclic compounds, wherein the heterocycle comprises one or more 5-6 membered rings containing oxygen and/or nitrogen. Such heterocycles may be saturated or unsaturated and substituted with groups selected from the aforementioned (A), (B), (C) and (D). The heterocycles are exemplified by piperazines, such as 2-methylpiperazine, N-(2-hydroxyethyl)-piperazine, 1,2-bis-(N-piperazinyl)ethane, and N,N'-bis(N-piperazinyl)piperazine, 2-methylimidazoline, 3-aminopiperidine, 2-aminopyridine, 2-(3-aminoethyl)-3-pyrroline, 3-aminopyrrolidine, N-(3-aminopropyl)-morpholide, etc. Among the heterocyclic compounds, the piperazines are preferred.

Typical polyamines that can be used to form the compounds of this invention include the following: ethylene diamine, 1,2-propylene diamine, 1,3-propylene diamine, diethylene triamine, triethylene tetramine, hexamethylene diamine, tetraethylene pentamine, methylaminopropylene diamine, N-(betaaminoethyl)piperazine, N,N'-di(betaaminoethyl)piperazine, N,N'-di(-beta-aminoethyl)-imidazolidone-2, N-(beta-cyanoethyl)ethane-1,2-diamine, 1,3,6,9-tetraaminooctadecane, 1,3,6-triamino-9-oxadecane, N-(beta-aminoethyl)diethanolamine, N-methyl-1,2-propanediamine, 2-(2-aminoethylamino)-ethanol 1,2-[2-(2-aminoethylamino)ethylamino]-ethanol.

Another group of suitable polyamines are the propyleneamines, (bisaminopropylethylenediamines). Propyleneamines are prepared by the reaction of acrylonitrile with an ethyleneamine, for example, an ethyleneamine having the formula $H_2N(CH_2CH_2NH)_ZH$ wherein Z is an integer from 1 to 5, followed by hydrogenation of the resultant intermediate. Thus, the product prepared from ethylene diamine and acrylonitrile would be $H_2N(CH_2)_3NH(CH_2)_2NH(CH_2)_3NH_2$.

In many instances the polyamine used as a reactant in the production of succinimides of the present invention is not a single compound but a mixture in which one or several compounds predominate with the average composition indicated. For example, tetraethylene pentamine prepared by the polymerization of aziridine or the reaction of dichloroethylene and ammonia will have both lower and higher amine members, e.g., triethylene tetramine, substituted piperazines and pentaethylene hexamine, but the composition will be largely tetraethylene pentamine and the empirical formula of the total amine composition will closely approximate that of tetraethylene pentamine. Finally, in preparing the succinimide for use in this invention, where the various nitrogen atoms of the polyamine are not geometrically equivalent, several substitutional isomers are possible and are encompassed within the final product. Methods of preparation of polyamines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volumes 2, pp. 99–116.

The reaction of a polyamine with an alkenyl or alkyl succinic anhydride to produce the polyamino alkenyl or alkyl succinimides is well known in the art and is disclosed in U.S. Pat. Nos. 2,992,708; 3,018,291; 3,024,237; 3,100,673; 3,219,666; 3,172,892 and 3,272,746. The above are incorporated herein by reference for their disclosures of preparing alkenyl or alkyl succinimides.

As noted above, the term "polyamino alkenyl or alkyl succinimide" refers to both polyamino alkenyl or alkyl mono- and bis-succinimides and to the higher analogs of alkenyl or alkyl poly succinimides. Preparation of the bis- and higher analogs may be accomplished by controlling the molar ratio of the reagents. For example, a product comprising predominantly mono- or bis-succinimide can be prepared by controlling the molar ratios of the polyamine and succinic anhydride. Thus, if one mole of polyamine is reacted with one mole of an alkenyl or alkyl substituted succinic anhydride, a predominantly mono-succinimide product will be prepared. If two moles of an alkenyl or alkyl substituted succinic anhydride are reacted per mole of polyamine, a bis-succinimide is prepared. Higher analogs may likewise be prepared.

A particularly preferred class of polyamino alkenyl or alkyl succinimides employed in the process of the instant invention may be represented by Formula II:

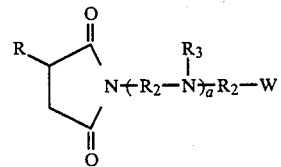

wherein R is alkenyl or alkyl of from 10 to 300 carbon atoms; $R_2$ is alkylene of 2 to 10 carbon atoms; $R_3$ is hydrogen, lower alkyl or lower hydroxy alkyl; a is an integer from 0 to 10; and W is —$NH_2$ or represents a group of Formula III:

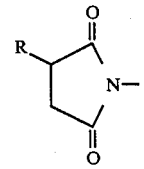

wherein R is alkenyl or alkyl of from 10 to 300 carbon atoms; with the proviso that when W is the group of Formula III above, then a is not zero and at least one of $R_3$ is hydrogen.

As indicated above, the polyamine employed in preparing the succinimide is often a mixture of different compounds having an average composition indicated as the Formula II. Accordingly, in Formula II each value of $R_2$ and $R_3$ may be the same as or different from other $R_2$ and $R_3$.

Preferably R is alkenyl or alkyl is preferably 10 to 200 carbon atoms and most preferably 20 to 100 carbon atoms.

Preferably R$_2$ is alkylene of 2 to 6 carbon atoms and most preferably is either ethylene or propylene.

Preferably, R$_3$ is hydrogen.

Preferably, a is an integer from 1 to 6.

In formula II, the polyamino alkenyl or alkyl succinimides may be conveniently viewed as being composed of three moieties that is the alkenyl or alkyl moiety R, the succinimide moiety represented by the formula:

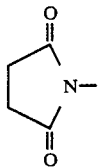

and the polyamino moiety represented by the group

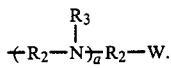

The preferred alkylene polyamines employed in this reaction are generally represented by the formula:

H$_2$N—R$_2$NH)$_a$—R$_2$NH$_2$ wherein R$_2$ is an alkylene moiety of 2 to 10 carbon atoms and a is an integer from about 0 to 10. However, the preparation of these alkylene polyamines do not produce a single compound and cyclic heterocycles, such as piperazine, may be included to some extent in the alkylene diamines.

B. POLYAMINO ALKENYL OR ALKYL SUCCINIMIDES WHEREIN ONE OR MORE OF THE NITROGENS IS SUBSTITUTED WITH HYDROCARBYL OXYCARBONYL, HYDROXY HYDROCARBYL OXYCARBONYL, OR HYDROXY POLY(OXYALKYLENE) OXYCARBONYL

The polyamino alkenyl of alkyl succinimides wherein one or more of the nitrogens of the polyamino moiety is substituted with a hydrocarbyl oxycarbonyl, or a hydroxy hydrocarbyl oxycarbonyl wherein said hydrocarbyl contains from 1 to about 20 carbon atoms and said hydroxy hydrocarbyl contains from 2 to about 20 carbon atoms may be prepared by reaction with a cyclic carbonate; by reaction with a linear mono- or poly-carbonate; or by reaction with a suitable chloroformate. Hydroxy poly(oxyalkylene) oxycarbonyl may be formed by reaction with a suitable chloroformate. The products so produced are effective dispersant and detergent additives for lubricating oils and for fuel.

Hydrocarbyl, as used in describing the hydrocarbyl oxycarbonyl components of this invention, denotes an organic radical composed of carbon and hydrogen which may be aliphatic, aromatic or combinations thereof, e.g., aralkyl. The hydrocarbyl group contains from about 1 to 20 carbon atoms, preferably 2 to 10 carbon atoms and most preferably 2 to 7 carbon atoms. Suitable hydrocarbyls are alkyls such as methyl, ethyl, propyl, butyl, isobutyl, pentyl, hexyl, octyl, etc.; alkenyls such as propenyl, isobutenyl, hexenyl, octenyl, etc.; aralkyl such as benzyl, and the like; aryls such as phenyl, naphthyl, and the like.

Hydroxy substituted hydrocarbyl, as used in describing the hydroxy hydrocarbyl oxycarbonyl components of this invention, denotes an organic radical composed of carbon and hydrogen containing 1 to 6 hydroxy groups, preferably 1 to 3, more preferably 1 to 2 hydroxy groups and most preferably 1 hydroxy group. It is also possible that some keto and aldehyde groups may be present in these hydroxy substituted hydrocarbyls. In the preferred embodiment the hydroxy hydrocarbyl does not contain ketone or aldehyde groups. The hydroxy substituted hydrocarbyl group contains from 2 to 20 carbon atoms, preferably 2 to 10 carbon atoms and most preferably 2 to 7 carbon atoms. Suitable hydroxy hydrocarbyls are hydroxy alkyls such as 2-hydroxyethyl, 3-hydroxypropyl, hydroxyisopropyl, 4-hydroxybutyl, 6-hydroxyhexyl, 2,3-dihydroxypropyl and the like. Some hydroxy alkyls may also be termed "hydroxyalkylene" such as 3-hydroxypropylene (HOCH$_2$CH$_2$CH$_2$—) and are included within the term hydroxy alkyls defined above. Other suitable hydroxyhydrocarbyls are hydroxy aralkyls such as 3-hydroxy-2-phenylpropyl

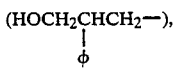

1-hydroxy-4,4'-diphenylene dimethylmethane

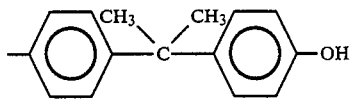

and the like.

Hydroxy poly(oxyalkylene), as used in describing the hydroxy poly(oxyalkylene) oxycarbonyl components of this invention, denotes a polymer containing from 2 to 30 C$_2$-C$_5$ oxyalkylene units and may be represented by the formula:

wherein alkylene is a C$_2$-C$_5$ alkyklene group and s is an integer from 2 to 30.

B(1) Cyclic Carbonates

The polyamino alkenyl or alkyl succinimide wherein one or more of the nitrogens of the succinimide is substituted with a hydroxy hydrocarbyl oxycarbonyl may be prepared by reaction of a polyamino alkenyl or alkyl succinimide with a cyclic carbonate. This reaction is conducted at a temperature sufficient to cause reaction of the cyclic carbonate with the polyamino alkenyl or alkyl succinimide. In particular, reaction temperatures of from about 0° C. to about 250° C. are preferred with temperatures of from about 100° C. to 200° C. being more preferred and temperatures of from 150° to 180° C. are most preferred.

The reaction may be conducted neat—that is, both the alkenyl or alkyl succinimide and the cyclic carbonate are combined in the proper ratio, either alone or in the presence of a catalyst, such as an acidic, basic or Lewis acid catalyst, and then stirred at the reaction temperature. Examples of suitable catalysts include, for instance, phosphoric acid, boron trifluoride; alkyl or aryl sulfonic acid, alkali or alkaline carbonate.

Alternatively, the reaction may be conducted in a diluent. For example, the reactants may be combined in a solvent such as toluene, xylene, oil or the like, and then stirred at the reaction temperature. After reaction completion, volatile components may be stripped off. When a diluent is employed, it is preferably inert to the reactants and products formed and is generally used in an amount sufficient to insure efficient stirring.

Water, which can be present in the polyamino alkenyl or alkyl succinimide, may be removed from the reaction system either before or during the course of the reaction via azeotroping or distillation. After reaction completion, the system can be stripped at elevated temperatures (100° C. to 250° C.) and reduced pressures to remove any volatile components which may be present in the product.

Another embodiment of the above process is a continuous system in which the alkenyl or alkyl succinic anhydride and polyamine are added at the front end of the system while the organic carbonate is added further downstream in the system.

In such a continuous system, the organic carbonate may be added at any time after mixing of the alkenyl or alkyl succinic anhydride with the polyamine has occurred. Preferably, the organic carbonate is added within two hours after mixing of the alkenyl or alkyl succinic anhydride with the polyamine, preferably after the major portion of the amine has reacted with the anhydride.

In a continuous system, the reaction temperature may be adjusted to maximize reaction efficiency. Accordingly, the temperature employed in the reaction of the alkyl or alkenyl succinic anhydride with a polyamine may be the same as or different from that which is maintained for the reaction of this resulting product with the cyclic carbonate. In such a continuous system, the reaction temperature is generally between 0°–250° C.; preferably between 125°–200° C.; and most preferably between 150°–180° C. Thus, another aspect of the instant invention is a continuous process which comprises (a) contacting at a temperature sufficient to cause reaction an alkenyl or alkyl succinic anhydride with a polyamine; and (b) then contacting at a temperature sufficient to cause reaction the product of (a) above with a cyclic carbonate.

Mole ratios of the cyclic carbonate to the basic amine nitrogen of the polyamino alkenyl or alkyl succinimide employed in the process of this invention are generally in the range of from about 0.2:1 to about 10:1; although preferably from about 0.5:1 to about 5:1; more preferably from 1:1 to 3:1 another preferred embodiment is 2:1.

The reaction is generally complete from with 0.5 to 10 hours.

Preferred cyclic carbonates include:

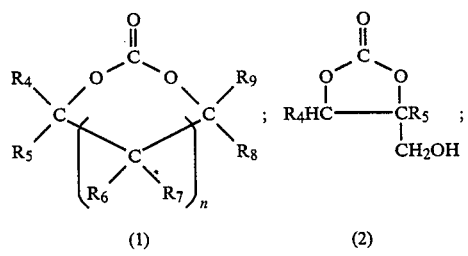

(1)  (2)

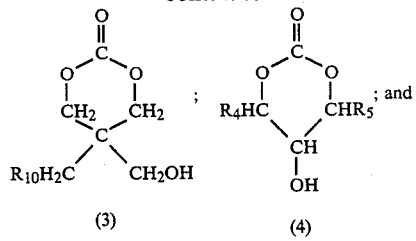

(3)  (4)

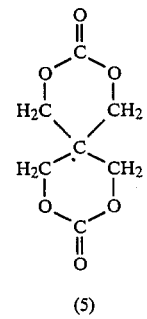

(5)

wherein $R_4$, $R_5$, $R_6$, $R_7$, $R_8$ and $R_9$ are independently selected from hydrogen or lower alkyl of 1 to 2 carbon atoms; $R^{10}$ is either hydrogen or hydroxy; and n is an integer from 0 to 1.

Preferred cyclic carbonates for use in this invention are those of formula 1 above. Preferred $R_4$, $R_5$, $R_6$, $R_7$, $R_8$ and $R_9$ are either hydrogen or methyl. Most preferably, $R_5$, $R_6$, $R_7$, $R_8$ and $R_9$ are hydrogen when n is one. $R_8$ is most preferably hydrogen or methyl while $R_4$, $R_5$, and $R_9$ are hydrogen when n is zero.

The following are examples of suitable cyclic carbonates for use in this invention: 1,3-dioxolan-2one(ethylene carbonate); 4-methyl-1,3-dioxolan-2-one(propylene carbonate); 4-hydroxymethyl-1,3-dioxolan-2-one; 4,5-dimethyl-1,3-dioxolan-2-one; 4-ethyl-1,3-dioxolan-2-one; 4,4-dimethyl-1,3-dioxolan-2-one; 4-methyl-5-ethyl-1,3-dioxolan-2-one; 4,5-diethyl-1,3-dioxolan-2-one; 4,4-diethyl-1,3-dioxolan-2-one; 1,3-dioxan-2-one; 4,4-dimethyl-1,3-dioxan-2-one; 5,5-dimethyl-1,3-dioxan-2-one; 5,5-dihydroxymethyl-1,3-dioxan-2-one; 5-methyl-1,3-dioxan-2-one; 4-methyl-1,3-dioxan-2-one; 5-hydroxy-1,3-dioxan-2-one; 5-hydroxymethyl-5-methyl-1,3-dioxan-2-one; 5,5-diethyl-1,3-dioxan-2-one; 5-methyl-5-propyl-1,3-dioxan-2-one; 4,6-dimethyl-1,3-dioxan-2-one; 4,4,6-trimethyl-1,3-dioxan-2-one and spiro [1,3oxa-2-cyclohexanone-5,5'-1', 3'- oxa-2'-cyclohexanone]. Other suitable cyclic carbonates may be prepared from sacchrides such as sorbitol, glucose, fructose, galactose and the like and from visconal diols prepared from $C_1$–$C_{30}$ olefins by methods known in the art.

Several of these cyclic carbonates are commercially available such as 1,3-dioxolan-2-one or 4-methyl-1,3-dioxolan-2-one. Cyclic carbonates may be readily prepared by known reactions. For example, reaction of phosgene with a suitable alpha alkane diol or an alkan-1,3-diol yields a carbonate for use within the scope of this invention as for instance in U.S. Pat. No. 4,115,206 which is incorporated herein by reference.

Likewise, the cyclic carbonates useful for this invention may be prepared by transesterification of a suitable alpha alkane diol or an alkan-1,3-diol with, e.g., diethyl carbonate under transesterification conditions. See, for instance, U.S. Pat. Nos. 4,384,115 and 4,423,205 which are incorporated herein by reference for their teaching of the preparation of cyclic carbonates.

As used herein, the term "alpha alkane diol" means an alkane group having two hydroxyl substituents wherein the hydroxyl substituents are on adjacent carbons to each other. Examples of alpha alkane diols include 1,2-propanediol, 2,3-butanediol and the like.

The term "alkan-1,3-diol" means an alkane group having two hydroxyl substituents wherein the hydroxyl substituents are beta substituted. That is, there is a methylene or a substituted methylene moiety between the hydroxyl substituted carbons. Examples of alkan-1,3-diols include propan-1,3-diol, pentan-2,4-diol and the like.

As used herein, the term "hydroxy hydrocarbyl oxycarbonyl" refers to the group hydroxy hydrocarbyl

the term "hydrocarbyloxy carbonyl" refers to the group hydrocarbyl

and the term "hydroxy poly(oxyalkylene) oxycarbonyl" refers" to the group

As used herein, the term "spiro[1,3-oxa-2-cyclohexanone-5 ,5'-1',3'-oxa-2'-cyclohexanone]" means the group

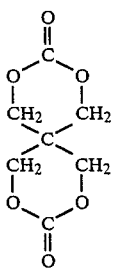

As used herein, the term "molar charge of cyclic carbonate (or chloroformate or linear carbonate) to the basic nitrogen of a polyamino alkenyl or alkylsuccinimide" means that the molar charge of cyclic carbonate (or chloroformate or linear carbonate) employed in the reaction is based upon the theoretical number of basic nitrogens contained in the succinimide. Thus, when 1 equivalent of triehylene tetraamine (TETA) is reacted with an equivalent of succinic anhydride, the resulting monosuccinimide will theoretically contain 3 basic nitrogens. Accordingly, a molar charge of 1 would require that a mole of cyclic carbonate (or chloroformate or linear carbonate) be added for each basic nitrogen or in this case 3 moles of cyclic carbonate for each mole of monosuccinimide prepared from TETA.

The alpha alkane diols, used to prepare the 1,3-dioxolan-2-ones employed in this invention, are either commercially available or may be prepared from the corresponding olefin by methods known in the art. For example, the olefin may first react with a peracid, such as peroxyacetic acid or hydrogen peroxide to form the corresponding epoxide which is readily hydrolyzed under acid or base catalysis to the alpha alkane diol. In another process, the olefin is first halogenated to a dihalo derivative and subsequently hydrolyzed to an alpha alkane diol by reaction first with sodium acetate and then with sodium hydroxide. The olefins so employed are known in the art.

The alkan-1,3-diols, used to prepare the 1,3-dioxan-2-ones employed in this invention, are either commercially available or may be prepared by standard techniques, e.g., derivatizing malonic acid.

4-Hydroxymethyl 1,3-dioxolan-2-one derivatives and 5-hydroxy-1,3-dioxan-2-one derivatives may be prepared by employing glycerol or substituted glycerol in the process of U.S. Pat. No. 4,115,206. The mixture so prepared may be separated, if desired, by conventional techniques. Preferably the mixture is used as is.

5,5-Dihydroxymethyl-1,3-dioxan-2-one may be prepared by reacting an equivalent of pentaerythritol with an equivalent of either phosgene or diethylcarbonate (or the like) under transesterification conditions.

5-hydroxymethyl-5-methyl-1,3-dioxan-2-one may be prepared by reacting an equivalent of trimethylolethane with an equivalent of either phosgene or diethylcarbonate (or the like) under transesterification conditions.

Spiro[1,3-oxa-2-cyclohexnnone-5,5'-1',3'-oxa-2'-cyclohexanone may be prepared by reacting an equivalent of pentaerythritol with two equivalents of either phosgene or diethylcarbonate (or the like) under transesterification conditions.

Cyclic carbonates of Formula I are used to illustrate the reaction of a cyclic carbonate with a polyamino alkenyl or alkyl succinimide. It is to be understood that the other cyclic carbonates employed in this invention react similarly. Cyclic carbonates may react with the primary and secondary amines of a polyamino alkenyl or alkyl succinimide to form two types of compounds. In the first instance, strong bases, including unhindered amines such as primary amines and some secondary amines, react with an equivalent of cyclic carbonate to produce a carbamic ester as shown in reaction (2) below:

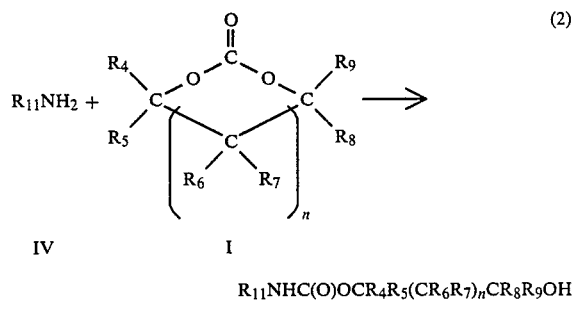

wherein $R_4$, $R_5$, $R_6$, $R_7$, $R_8$, $R_9$ and n are as defined above and $R_{11}$ is the remainder of a polyamino alkenyl or alkyl succinimide. In this reaction, the amine nitrogen has been rendered nonbasic by formation of the carbamate, V.

In the second instance, hindered bases, such as hindered secondary amines, may react with an equivalent of the same cyclic carbonate to form a hydroxyalkyleneamine linkage with the concomitant elimination of $CO_2$ as shown below in reaction (3):

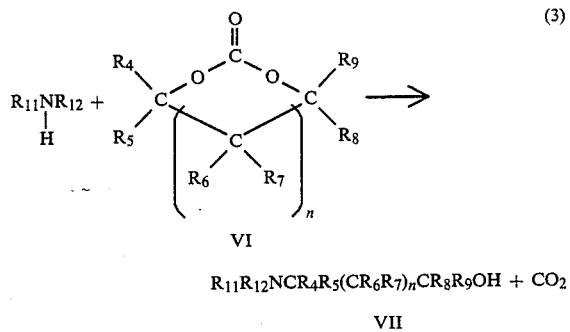

$R_{11}R_{12}NCR_4R_5(CR_6R_7)_nCR_8R_9OH + CO_2$

VII wherein $R_4$, $R_5$, $R_6$, $R_7$, $R_8$, $R_9$, $R_{11}$ and n are as defined above and $R_{12}$ is an alkyl or alkylene linking group which hinders the amine. Unlike the carbamate products of reaction (1), the hydroxyalkyleneamine products of reaction (2) retain their basicity. These hydroxyalkyleneamine derivatives, VII, (when n=0) are believed to be similar to those which are produced by the addition to an alkenyl or alkyl succinimide of a substituted ethylene oxide of the formula:

wherein $R_4$, $R_5$, $R_6$ and $R_7$ are as defined above. (See for instance U.S. Pat. Nos. 3,367,943 and 3,377,111).

In theory, if only primary and secondary amines are employed in the polyamine moiety of the succinimide a determination of whether the carbonate addition follows reaction (1) or reaction (2) could be made by monitoring the AV (alkalinity value or alkalinity number - refers to the amount of base as milligrams of KOH in 1 gram of a sample) of the product. Accordingly, if the reaction proceeded entirely via reaction (1) above, a reaction product prepared by reacting an equivalent of carbonate for each basic nitrogen should yield an AV of zero. That is to say that all the basic amines in the polyamine moiety have been converted to nonbasic carbamates.

However, as previously noted, alkylene polyamines such as triethylene tetraamine and tetraethylene pentamine (e.g., tetraethylenepentaamine-TEPA and triethylenetetramine-TETA), contain tertiary amines (piperazines, etc.) which may account for as much as 30% of the basic nitrogen content. Although Applicant does not want to be limited to any theory, it is believed that these tertiary amines, although basic, are not reactive with the carbonate. Accordingly, even if the reaction proceeded entirely by reaction (1) above, an AV of approximately 30% of the original AV may be retained in the final product. Nevertheless, a large drop in the AV of the product is significant evidence that a substantial portion of the reaction product contains carbamic esters.

In fact, the addition of approximately one equivalent of ethylene carbonate for each basic nitrogen appreciably lowers the AV for the monosuccinimide (1), for the bis-succinimide (2), and for the mono-succinimide (3). This indicates that a substantial portion of the firt equivalent of ethylene carbonate is adding to the succinimide via reaction (1) yielding hydroxy hydrocarbyl carbamic esters.

1. Succinimide (1) is the product obtained from the reaction of triethylenetetramine (TETA) and polyisobutenyl succinic anhydride (average MW=1050) wherein the molar charge of TETA to the polyisobutenyl succinic anhydride is 0.90. Diluent oil is then added to obtain a concentration of approximately 50 percent actives.
2. Succinimide (2) is the product obtained from the reaction of tetraethylene pentamine (TEPA) and polyisobutenyl succinic anhydride (Average MW=1050). The molar charge of TEPA to the polyisobutenylsuccinic anhydride is 0.5 which gives a bissuccinimide. Diluent oil is then added to obtain a concentration of approximately 50 percent actives.
3. Succinimide (3) is the reaction product obtained from tetraethylene pentamine (TEPA) and polyisobutenyl succinic anhydride (Average MW=1050). The molar charge of TEPA to the polyisobutenyl succinic anhydride is 0.87 which gives a mono-succinimide. Diluent oil is then added to obtain a concentration of approximately 50 percent actives.

On the other hand, the addition of a second equivalent of ethylene carbonate in these reactions does not result in appreciably further lowering of the AV. This suggests that the additional carbonate either reacts via reaction (2) above, if reactive amino nitrogen is available, to form hydroxyalkyleneamine groups or are reacting with the hydroxyl group of the carbamate as shown in reaction 4(a) below:

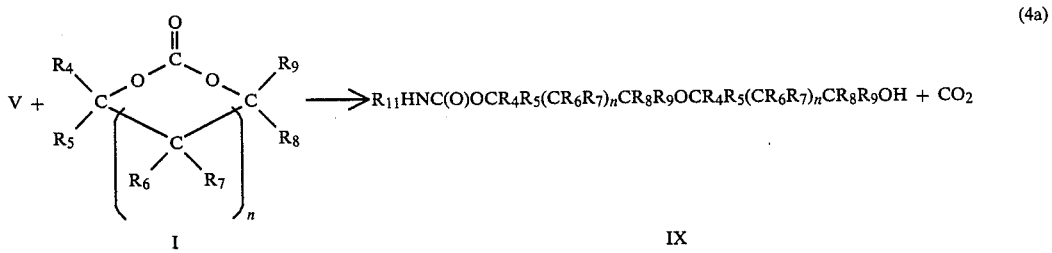

wherein $R_4$, $R_5$, $R_6$, $R_7$, $R_8$, $R_9$, $R_{11}$ and n are as defined above. The process of reaction 4a allows for additional carbonate to add to the hydroxyl group of product IX to form a hydroxy tri(oxyalkylene) carbamate as shown in reaction 4(b) below:

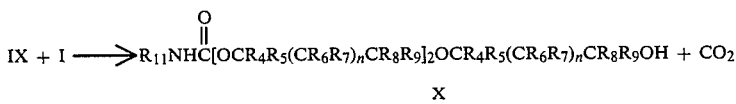

$$IX + I \longrightarrow R_{11}NHC[OCR_4R_5(CR_6R_7)_nCR_8R_9]_2OCR_4R_5(CR_6R_7)_nCR_8R_9OH + CO_2 \quad (4b)$$

X wherein $R_4$, $R_5$, $R_6$, $R_7$, $R_8$, $R_9$ and $R_{11}$ are as defined above. As is apparent from the above reaction, the poly(oxyalkylene) portion of the carbamate can be repeated several times, generally up to 10 times or more, simply by addition of more carbonate to form a hydroxy poly(oxyalkylene) carbamate.

Likewise, additional equivalents of carbonate could equally add to the hydroxyl group of the hydroxyalkyleneamine derivative, VII, of reaction (3) as shown in reaction (5) below:

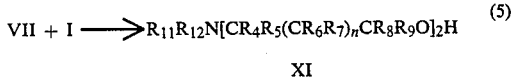

$$VII + I \longrightarrow R_{11}R_{12}N[CR_4R_5(CR_6R_7)_nCR_8R_9O]_2H \quad (5)$$

XI wherein $R_4$, $R_5$, $R_6$, $R_7$, $R_8$, $R_9$, $R_{11}$ and $R_{12}$ are as defined above. Repeating the process of reaction (5) above by the addition of increasing amounts of carbonate produces a hydroxyalkylenepoly(oxyalkylene)amine derivative of Formula XII below:

$$R_{11}R_{12}N[CR_4R_5(CR_6R_7O)_nCR_8R_9]_yH \qquad XII$$

wherein $R_4$, $R_5$, $R_6$, $R_7$, $R_8$, $R_9$, $R_{11}$ and $R_{12}$ and n are as defined above and y is an integer from 3 to 10.

It is also contemplated that reactions (4) and (5) above may also produce acyclic carbonate linkages with the terminal hydroxyl group. Likewise, if $R_{11}$ (or $R_{12}$) is hydrogen, then an additional hydroxyalkylene could add to the amino group.

Accordingly, it is expected that the reaction of a cyclic carbonate with a polyamino alkenyl or alkyl succinimide will yield a mixture of products. When the molar charge of the cyclic carbonate to the basic nitrogen of the succinimide is about 1 or less, it is anticipated that a large portion of the primary and secondary amines of the succinimide will have been converted to hydroxy hydrocarbyl carbamic esters with some hydroxyhydrocarbylamine derivatives also being formed. As the mole ratio is raised above 1, poly(oxyalkylene) polymers of the carbamic esters and the hydroxyhydrocarbylamine derivatives are expected.

It is expected that use of the spiro[1,3-oxa-2-cyclohexanone-5,5'-1',3'-oxa-2'-cyclohexanone] may yield internally cyclized products and also bring about crosslinking between two succinimides.

In some instances, it may be desirable to increase the proportion of carbamic esters formed in these reactions. This may be accomplished by changing reaction conditions such as temperature or the rate of addition of cyclic carbonate, etc. or employing a polyamine with a large percentage of primary amine. Another method may be to employ alkyl-substituted (i.e., one or more of $R_1$, $R_2$, $R_3$, $R_4$, $R_5$, or $R_6$ is alkyl) or hydroxyalkyl substituted carbonates. Still another method would be to employ a 6-membered ring cyclic carbonate.

B(2) Linear Mono- or Polycarbonates

Linear carbonates react with a basic nitrogen of a polyamino alkenyl or alkyl succinimide to form carbamates. Suitable linear carbonates include both monocarbonates of formula XIII and polycarbonates of formula XIV:

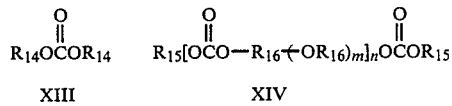

$$R_{14}OCOR_{14} \qquad R_{15}[OCO-R_{16}(-OR_{16})_m]_nOCOR_{15}$$

XIII  XIV wherein $R_{14}$ is independently hydrocarbyl of from 1 to about 20 carbon atoms; $R_{15}$ is hydroxy hydrocarbyl of from 2 to 20 carbon atoms; $R_{16}$ is a divalent hydrocarbyl group of from 2 to 20 carbon atoms, m is an integer from 0 to 10 or more; n is an integer of from 1 to 200.

Preferably $R_{14}$ is hydrocarbyl of from 1 to 10 carbon atoms; $R_{15}$ is hydroxy hydrocarbyl of from 2 to 10 carbon atoms; $R_{16}$ is a divalent hydrocarbyl of from 2 to 10 carbon atoms; and n is preferably an integer from 1 to 100 and most preferably 1 to 10.

Monocarbonates, XIII, are believed to react with primary or secondary amines of a polyamino alkenyl or alkyl succinimide, with the concommittant elimination of the alcohol, $R_{14}OH$, as shown in reaction (6) below:

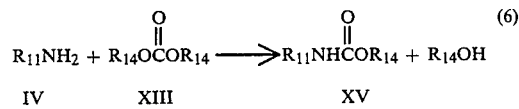

$$R_{11}NH_2 + R_{14}OCOR_{14} \longrightarrow R_{11}NHCOR_{14} + R_{14}OH \quad (6)$$

IV  XIII  XV wherein $R_{11}$ and $R_{14}$ are as defined above.

Reaction (6) is conducted by contacting the monocarbonate with a polyamino alkenyl or alkyl succinimide. The reaction is conducted at a temperature sufficient to cause reaction of the monocarbonate with the polyamino alkenyl or alkyl succinimide. In particular, reaction temperatures of from about 100° C. to about 250° C. are preferred with temperatures of from about 150° C. to 250° C. being most preferred.

The reaction may be conducted neat—that is, both the polyamino alkenyl or alkyl succinimide and the carbonate are combined in the proper ratio, either alone or in the presence of a catalyst, such as an acidic, basic or Lewis acid catalyst, and then stirred at the reaction temperature. Examples of suitable catalysts include, for instance, phosphoric acid, boron trifluoride, alkyl or aryl sulfonic acid, alkali or alkaline carbonate.

Alternatively, the reaction may be conducted in a diluent. For example, the reactants may be combined in a solvent such as toluene, xylene, oil or the like, and then stirred at the reaction temperature. After reaction completion, volatile components may be stripped off. When a diluent is employed, it is preferably inert to the reactants and products formed and is generally used in an amount sufficient to insure efficient stirring.

Water, which can be present in the polyamino alkenyl or alkyl succinimide, may be removed from the reaction system either before or during the course of the reaction via azeotroping or distillation. After reaction completion, the system can be stripped at elevated temperatures (100° C. to 250° C.) and reduced pressures to remove any volatile components which may be present in the product.

Another embodiment of the above process is a continuous flow system in which the alkenyl or alkyl succinic anhydride and polyamine are added at the front end of the flow while the hydrocarbyl carbonate is added further downstream in the system.

Mole ratios of the hydrocarbyl carbonate to the basic amine nitrogen of the polyamino alkenyl or alkyl succinimide employed in the process of this invention are generally in the range of from about 0.2:1 to about 1:1; preferably 0.5:1 to about 1:1 and most preferably 0.7:1 to about 1:1.

The reaction is generally complete from within 0.5 to 10 hours.

Suitable monocarbonates, XIII, may be prepared by transesterifying diethyl carbonate or a similar material using conditions well known in the art. Suitable monocarbonates include dimethyl carbonate, diethyl carbonate, di-n-propyl carbonate, diisopropylcarbonate, diphenyl carbonate, di-n-butyl carbonate, dibenzyl carbonate, and the like.

Linear polycarbonates are of the general formula:

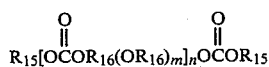
$$R_{15}[OCOR_{16}(OR_{16})_m]_nOCOR_{15} \quad \text{XIV}$$

wherein $R_{15}$, $R_{16}$, m and n as defined above. These polycarbonates react with a primary or secondary amine of the polyamino alkenyl or alkyl succinimide to form a carbamate as shown in reaction (7) below wherein for the sake of illustration m is limited to 0:

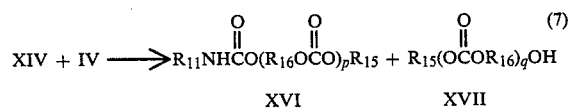
$$XIV + IV \longrightarrow R_{11}NHCO(R_{16}OCO)_pR_{15} + R_{15}(OCOR_{16})_qOH \quad (7)$$
$$\qquad\qquad\qquad XVI \qquad\qquad\qquad XVII$$

wherein $R_{11}$, $R_{15}$ and $R_{16}$ are as defined above and p and q are integers such that p+q=n. Further reaction of the polycarbonate, with another primary or secondary amine of the polyamino alkenyl or alkyl succinimide will split off additional units of carbonate from either XVI or XVII. Accordingly, continued reaction of the polycarbonate with the polyamino alkenyl or alkyl succinimide reduces the size of the polycarbonate until either no additional reactive amine nitrogens are available to react with the carbonate or each carbonate unit of the polycarbonate has been reacted with a primary or secondary amine to form a compound of the formula:

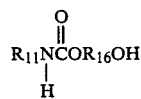
$$\underset{H}{R_{11}N}COR_{16}OH \quad \text{XVIII}$$

wherein $R_{11}$ and $R_{16}$ are as defined above. By controlling the amount of polycarbonate employed so that the total number of carbonate units contained therein is less than the total number of available primary and secondary amines, the carbamates of formula XVIII will be formed. If excess polycarbonate is employed such that the total number of carbonate units is greater than the total number of available primary and secondary amines, carbamates of formula, XVI, which contain one or more carbonate units, are formed. These carbamates are useful dispersants and detergents and may be added to the lubricating oil or fuel as is. Alternatively, the carbamates of formula XVI may be treated with an excess of alcohol such as ethanol at elevated temperatures under transesterification conditions to remove the carbonate functions in formula XVI as shown in reaction (8) below:

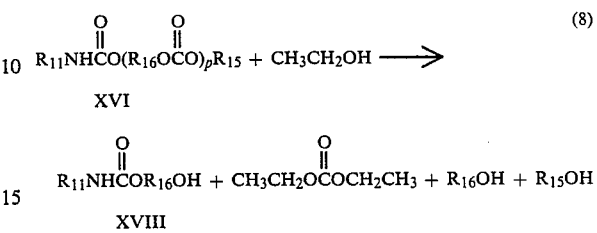
$$R_{11}NHCO(R_{16}OCO)_pR_{15} + CH_3CH_2OH \longrightarrow \quad (8)$$
$$XVI$$
$$R_{11}NHCOR_{16}OH + CH_3CH_2OCOCH_2CH_3 + R_{16}OH + R_{15}OH$$
$$XVIII$$

The carbamates of formula XVIII may be post-treated with a cyclic carbonate such as ethylene carbonate to form a hydroxy polyoxyalylene derivative similar to that of formula X above.

Reaction (7) is conducted at a temperature sufficient to cause reaction of the polycarbonate, XIV, with the polyamino alkenyl or alkyl succinimide, IV. In particular, reaction temperatures of from about 0° C. to about 250° C. are preferred with temperatures of from about 100° C. to 200° C. being most preferred.

The reaction may be conducted neat—that is, both the polyamino alkenyl or alkyl succinimide and the polycarbonate are combined in the proper ratio, either alone or in the presence of a catalyst, such as an acidic, basic or Lewis acid catalyst, and then stirred at the reaction temperature. Examples of suitable catalysts include, for instance, phosphoric acid, boron trifluoride, alkyl or aryl sulfonic acid, alkali or alkaline carbonate.

Alternatively, the reaction may be conducted in a diluent. For example, the reactants may be combined in a solvent such as toluene, xylene, oil or the like, and then stirred at the reaction temperature. After reaction completion, volatile components may be stripped off. When a diluent is employed, it is preferably inert to the reactants and products formed and is generally used in an amount sufficient to insure efficient stirring.

Water, which can be present in the polyamino alkenyl or alkyl succinimide, may be removed from the reaction system either before or during the course of the reaction via azeotroping or distillation. After reaction completion, the system can be stripped at elevated temperatures (100° C. to 250° C.) and reduced pressures to remove any volatile components which may be present in the product.

Another embodiment of the above process is a continuous flow system in which the alkenyl or alkyl succinic anhydride and polyamine are added at the front end of the flow while the polycarbonate is added further downstream in the system.

Mole ratios of the individual carbonate units of polycarbonate to the basic amine nitrogen of the polyamino alkenyl or alkyl succinimide employed in the process of this invention are generally in the range of from about 0.1:1 to about 5:1 although preferably from about 0.5:1 to about 1:1.

The reaction is generally complete from within 0.5 to 10 hours.

Suitable polycarbonates may be prepared as described in U.S. Pat. No. 4,423,205. This patent is incorporated herein by reference for its teaching of the preparation of polycarbonates.

In preparing the polycarbonates of formula XIV, an excess of a suitable hydrocarbyl glycol, such as ethylene glycol, propylene glycol and the like, is added to a dihydrocarbyl carbonate, such as diethylcarbonate, under transesterification conditions to theoretically produce the polycarbonates of formula XIV(a) (i.e. m=0)

XIV(a)

However, in practice, carbon dioxide is evolved during this reaction and the resulting polycarbonate contains some oxyhydrocarbyl content as shown below:

wherein m is an integer generally from 0 to 10 or more and hydrocarbyl is derived the hydrocarbyl glycol employed. The amount of oxyhydrocarbyl content between the n carbonate units varies from carbonate unit to carbonate unit.

Preferred polycarbonates for use in this invention are those wherein $R_{15}$ is hydroxyalkylene and $R_{16}$ is alkylene wherein alkylene is from 2 to 10 carbon atoms; preferably 2 to 5 carbon atoms. Other preferred polycarbonates are those wherein $R_{15}$ is HO-Aryl-$R_{17}$-Aryl- and $R_{16}$ is -Aryl-$R_{17}$-Aryl- wherein $R_{17}$ is alkylene of from 2 to 5 carbon atoms and aryl is a $C_6$ to $C_{10}$ aryl. Suitable aryls include benzyl ad naphthyl.

B(3) Chloroformates

Chloroformates and other haloformates react with a primary or secondary amine nitrogen of a polyamino alkenyl or alkyl succinimide to form carbamates. Suitable chloroformates include hydrocarbyl chloroformates of formula XIX below; hydroxy protected hydrocarbyl chloroformates of formula XX below and hydroxy protected poly(oxyalkylene) chloroformates of formula XXI:

 XIX

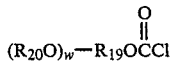 XX

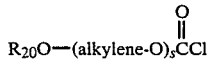 XXI wherein w is an integer from 1 to 6; $R_{18}$ is hydrocarbyl of from 1 to 20 carbon atoms, $R_{19}$ is hydrocarbyl of 2 to 20 carbon atoms, $R_{20}$ is a hydroxy protecting group, alkylene is a $C_2$-$C_5$ alkylene group and s is an integer from 2 to 30, preferably 2 to 20.

The chloroformates of formulas XIX, XX and XXI react with a primary or secondary amine to form a carbamate as shown in reaction (9) below:

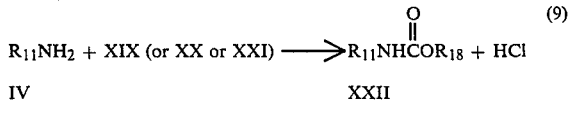

wherein $R_{11}$ and $R_{18}$ are as defined above.

Reaction (9) is conducted by contacting the chloroformate, XIX (or XX or XXI), with the polyamino alkenyl or alkyl succinimide, IV. The reaction may be conducted neat or in a suitable inert diluent. Suitable diluents include ethyl acetate, toluene, xylene, oil and the like. An organic base such as pyridine, triethylamine and the like may be added to the reaction to scavenge the acid generated. However, the generated acid is preferably removed by an alkaline water wash (pH of from 8-9) or an alkaline brine wash (pH 8-9) of the reaction solution after reaction completion without the need of added base. The reaction is generally conducted at from −78° C. to 50° C. with 0°-30° C. being preferred. However, when chloroformate XX or XXI is employed, and the protecting $R_{20}$ group is trichloroacetate, use of lower temperatures, i.e., −78° C. to 0° C. help prevent possible side products from forming and may be preferred for this purpose. The reaction is generally complete from within 0.5 to 24 hours. However, if the polyamino moiety of the alkenyl or alkyl succinimide contains hydroxyalkyl substitution, it is preferable to conduct reaction (9) at a sufficiently low temperature to prevent reaction of the chloroformate with the hydroxy group resulting in carbonate formation. Generally, temperatures of from −78° C. to 0° C. are sufficiently low to minimize this carbonate formation. In any event, any carbonate so formed from the hydroxyalkyl group during the chloroformate reaction may itself react with a primary or secondary amino nitrogen of the succinimide or may be readily removed by post-treating the product with an alkanol (e.g., ethanol) under transesterification conditions.

After the water washing, the product may be further isolated by conventional techniques such as chromatography, filtration and the like or used in reaction (10) without additional isolation.

The hydroxy protecting group, $R_{20}$, used in chloroformate, XX and XXI, is any acceptable hydroxy protecting groups which do not contain a functionality which is reactive with a chloroformate or an amine of the succinimide under the reaction conditions. Suitable protecting groups include benzyl, carbobenzoxy

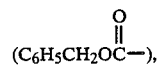

trichloroacetyl

and the like. The identity of the particular protecting group is not critical provided it can be readily removed from the hydroxy group after reaction (9) is completed. For instance, trichloroacetyl may be removed by an alkaline brine wash (pH of from 8-9); by addition of a dialkylamine (e.g., dimethylamine into the reaction medium; or di-n-butylamine) or by an aqueous solution of tetrahydrofuran containing approximately 30% water at a pH 9-10, conducted at the completion of reaction (9) as shown in reaction (10) below:

$$R_{11}NHCOR_{19}(OR_{20})_w \xrightarrow[R_{20} \text{ protecting group}]{\text{removal of the}}$$ (10)

XXIII $$R_{11}NHCOR_{19}(OH)_w$$

XXIV

More extreme reaction conditions (i.e. higher temperature or pH >9-10) may result in product decomposition. Removal of other $R_{20}$ protecting groups is well known in the art. For example, benzyl and carbobenzoxy protecting groups may be readily removed by hydrogenation using a suitable catalyst such as palladium on carbon. Similarly, carbobenzoxy protecting groups may also be removed by trifluoroacetic acid.

If additional chloroformate, XIX, XX, or XXI is added to the reaction it will react with any available primary or secondary amine of the polyamine alkenyl or alkyl succinimide and convert these to carbamates. Preferably, it is desirable to convert at least 20% of the primary and secondary amines to carbamates; more preferably at least 50% of the primary and secondary amines should be converted to carbamates; and most preferably all of the primary and secondary amines to carbamates.

In general, maximum carbamate formation in the polyamino alkenyl or alkyl succinimide can be obtained by employing a molar charge of chloroformate to the theoretical basic nitrogen of the alkenyl or alkyl succinimide of from 0.7:1 to about 1:1. In some cases, a slight excess of chloroformate may be employed to enhance reaction rate.

Suitable chloroformates of formula XIX include $C_1$ to $C_{20}$ alkyl chloroformates prepared from the corresponding alcohol by reaction with phosgene. The alcohols are either commercially available or may be readily prepared by reduction of the corresponding carboxylic acid by art recognized techniques.

Suitable chloroformates of formula XX wherein w=1 may be prepared as shown in reactions (11) and (12) below. In these reactions the protecting group $R_{20}$ is trichloroacetyl although it is understood that other suitable protecting groups may be similarly employed.

$$HO-R_{19}-OH + Cl_3CCOH \longrightarrow Cl_3CCOR_{19}OH + H_2O$$ (11)

XXV  XXVI  XXVII $$XXVII + ClCCl \longrightarrow Cl_3CCOR_{19}OCCl + HCl$$ (12)

XXVIII  XXIX wherein $R_{19}$ is as defined above.

Reaction (11) is a conventional esterification reaction and is conducted by combining the diol, XXV, with the acid XXVI, to yield the monester, XXVII. In order to prevent formation of a diester, an excess of diol, XXV, is employed. In general, from 1.1 to 4 equivalents of diol, XXV, and preferably 2 equivalents per equivalent of acid XXVI are employed in reaction (11) although larger excesses may be employed. The reaction may be conducted neat or in a suitable diluent such as toluene, benzene and the like. The water generated during the reaction may be readily removed via a Dean-Stark trap. The product ester, XXVII, may be isolated by conventional techniques such as chromatography, filtration and the like.

Alternatively, the monoester, XXVII, may be prepared by forming the diester of glycol XXV and then hydrolyzing one of the esters to the alcohol to form monoester XXVII.

Reaction (12) is conducted by adding the ester, XXVII, to a suitable inert diluent such as toluene, benzene and the like. Phosgene, XXVIII, is then added to the system over a period of time. Generally, an excess of phosgene is employed. In particular, from approximately 1.1-2.5 equivalents of phosgene is added per equivalent of ester, XXVII. The reaction is conducted at from $-10°$ to $10°$ C. and is generally complete from within ½ to 12 hours. If it is necessary to prevent formation of side products, the ester, XXVII, may be slowly added to an excess of phosgene XXVIII. The chloroformate, XXIX, may be isolated by conventional techniques such as distillation but preferably the system is stripped of a portion of the inert diluent which also removes the hydrochloride gas generated. The product XXVIII, and the remaining diluent are then used as is in reaction (9) above.

The glycol, XXV, is either commercially available or may be readily prepared from art recognized techniques.

When w is 2 or more, the chloroformate, XX, is prepared similarly as to reactions (11) and (12) above. However, it is noted that excess polyol in these reactions is not necessary since all but one of the hydroxy groups of the polyol should be protected. Accordingly, if the polyol contains 4 hydroxy groups, three of these should be protected. This can be accomplished by using 3 equivalents of the protecting agent such as trichloroacetic acid. Alternatively, the triester may be prepared by first forming the tetraester and then hydrolyzing one of these esters to a hydroxy group to form the triester. In any case, a mixture is obtained from both procedures and the desired product being isolated by conventional techniques (i.e., chromatography).

Polyols are either commercially available (i.e. glycerol, pentaerythritol, etc.) or may be readily prepared by art recognized techniques.

Chloroformates of formula XXI are prepared similarly as those of formula XX by substituting a poly(oxyalkylene) glycol, XXX, in reactions (10) and (11) above.

$$HO+alkyleneO)_sH$$
XXX wherein alkylene and s are as defined above.

The poly(oxyalkylene) glycol materials, XXX, are the addition polymers of lower aliphatic oxides such as ethylene oxide, propylene oxide, the butylene oxides and the pentylene oxides, and are prepared by employing a glycol such as ethylene glycol, propylene glycol and the like under polymerization conditions. These materials are commercially available or may be readily prepared.

In the polymerization reaction, a single type of alkylene oxide may be employed, e.g., propylene oxide, in which case the product is a homopolymer, e.g., a poly(oxypropylene) propanol. However, copolymers are equally satisfactory and random copolymers are readily prepared by contacting the hydroxyl-containing compound with a mixture of alkylene oxides, such as a mixture of propylene and butylene oxides. Block copolymers of oxyalkylene units also provide satisfactory poly(oxyalkylene) polymers for the practice of the present invention.

In general, the poly(oxyalkylene) polymers are mixtures of compounds that differ in polymer chain length. However, their properties closely approximate those of the polymer represented by the average composition and molecular weight.

If the polyamino moiety of the alkenyl or alkyl succinimide does not contain hydroxy alkyl substitution, hydroxy alkyl groups may be introduced into the modified succinimides of this invention by addition of a chloroalkanol (e.g., chloroethanol) provided the succinimide retains some basic nitrogen. The chloroalkanol will react with basic nitrogen to yield the hydroxy alkyl group. This reaction may also produce some quaterinized nitrogen products but this may be minimized by controlling the reaction conditions such as by limiting the amount of chloroalkanol added.

Alternatively, the hydroxy hydrocarbyl carbamates may be prepared by reacting the succinimide with an epoxide or hydrocarbyl hydroxy chloride in the presence of $CO_2$. Accordingly, by employing chloroformate, XIX, XX, or XXI, and a polyamino alkenyl or alkyl succinimide of formula II above in the above reactions, compounds of the following formula are produced.

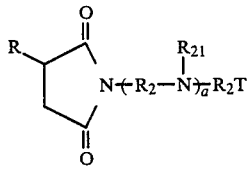     XXXI wherein R is alkenyl or alkyl of from 10 to 300 carbon atoms $R_2$ is alkylene of 2 to 10 carbon atoms; $R_{21}$ is hydrogen; lower alkyl of from 1 to 6 carbon atoms, lower hydroxy alkyl of from 1 to 6 carbon atoms,

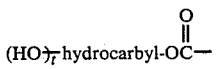

wherein t is an integer from 0 to 6, and hydrocarbyl is a hydrocarbyl group of from 2 to 20 carbon atoms; and

wherein alkylene-O is a $C_2$–$C_5$ oxyalkylene and s is an integer from 2 to 30; a is an integer of from 0 to 10; and T is —$NH_2$,

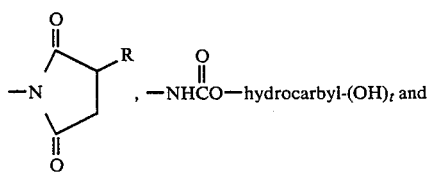, —NHCO—hydrocarbyl-(OH)$_t$ and

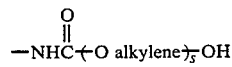

wherein R, hydrocarbyl, alkylene, s and t are as defined above; with the proviso that if T is —$NH_2$ or

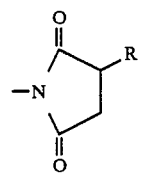

then a is not zero and at least one of $R_{21}$ is either

Preferably R is alkenyl or alkyl of from about 12 to 100 carbon atoms; $R_2$ is alkylene of from 2 to 6 carbon atoms; a is an integer of from 1 to 6; $R_{21}$ is

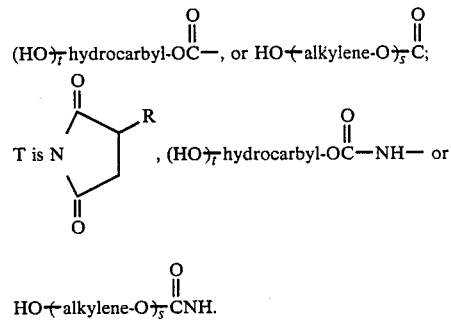

Preferably t is an integer of from 1 to 6, more preferably 1 to 3, most preferably 1. Carbon atoms having 2 hydroxy groups are hemiketals which readily lose water to form ketones (or aldehydes). For the purpose of this invention, if t is 2 or more then the hydroxy groups are not on the same carbon atom. Moreover, the carbon atom attached to the carbamate cannot be substituted with hydroxy since such hydroxy substitution would require that the starting alcohol XXV (or its equivalent if t is greater than 1) be a hemiketal which is not within the scope of this invention.

In still another aspect of this invention, the hydroxy hydrocarbyl carbamates of formula V, XVIII, XXIII and the like may be post-treated with an alkenyl or alkyl succinic anhydride of the formula:

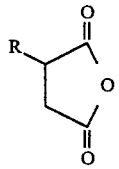

wherein R is alkenyl or alkyl of from about 10 to 300 carbon atoms.

The reaction is generally conducted by combining the hydroxy hydrocarbyl carbamate and the alkenyl or alkyl succinic anhydride. The reaction may be conducted neat but preferably on an inert diluent such as toluene, xylene, oil or the like is employed. The reaction is generally conducted at from 50° to 250° C., preferably 100°–200° C. and most preferably 150°–180° C. and is generally complete from within 1 to 24 hours. After reaction completion, the system can be stripped at elevated temperatures and reduced pressures to remove any volatile components which may be present in the product.

Generally, from about 0.1 to 1.5 equivalents of an alkenyl or alkyl succinic anhydride per equivalent of modified polyamino alkenyl or alkyl succinimide is employed, although preferably from about 0.5 to 1.0. In some cases higher amounts (>1.5 equivalents) may be used.

The modified succinimides of this invention can also be reacted with boric acid or a similar boron compound to form borated dispersants having utility within the scope of this invention. In addition to boric acid (boron acid), examples of suitable boron compounds include boron oxides, boron halides and esters of boric acid. Generally from about 0.1 equivalents to 10 equivalents of boron compound to the modified succinimide may be employed.

The modified polyamino alkenyl or alkyl succinimides of this invention are useful as detergent and dispersant additives when employed in lubricating oils. When employed in this manner, the modified polyamino alkenyl or alkyl succinimide additive is usually present in from 0.2 to 10 percent by weight to the total composition and preferably at about 0.5 to 5 percent by weight. The lubricating oil used with the additive compositions of this invention may be mineral oil or synthetic oils of lubricating viscosity and preferably suitable for use in the crankcase of an internal combustion engine. Crankcase lubricating oils ordinarily have a viscosity of about 1300 CSt 0° F. to 22.7 CSt at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Additive concentrates are also included within the scope of this invention. The concentrates of this invention usually include from about 90 to 10 weight percent of an oil of lubricating viscosity and from about 10 to 90 weight percent of the complex additive of this invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although an oil of lubricating viscosity may be used.

Other additives which may be present in the formulation include rust inhibitors, foam inhibitors, corrosion inhibitors, metal deactivators, pour point depressants, antioxidants, and a variety of other wellknown additives.

It is also contemplated the modified succinimides of this invention may be employed as dispersants and detergents in hydraulic fluids, marine crankcase lubricants and the like. When so employed, the modified succinimide is added at from about 0.1 to 10 percent by weight to the oil. Preferably, at from 0.5 to 5 weight percent.

When used in fuels, the proper concentration of the additive necessary in order to achieve the desired detergency is dependent upon a variety of factors including the type of fuel used, the presence of other detergents or dispersants or other additives, etc. Generally, however, and in the preferred embodiment, the range of concentration of the additive in the base fuel is 10 to 10,000 weight parts per million, preferably from 30 to 2,000 weight parts per million, and most preferably from 30 to 700 parts per million of the modified succinimide per part of base fuel. If other detergents are present, a lesser amount of the modified succinimide may be used.

The modified succinimide additives of this invention may be formulated as a fuel concentrate, using an inert stable oleophilic organic solvent boiling in the range of about 150° to 400° F. Preferably, an aliphatic or an aromatic hydrocarbon solvent is used, such as benzene, toluene, xylene or higher-boiling aromatics or aromatic thinners. Aliphatic alcohols of about 3 to 8 carbon atoms, such as isopropanol, isobutylcarbinol, n-butanol and the like, in combination with hydrocarbon solvents are also suitable for use with the fuel additive. In the fuel concentrate, the amount of the additive will be ordinarily at least 10 percent by weight and generally not exceed 70 percent by weight and preferably from 10 to 25 weight percent.

The following examples are offered to specifically illustrate this invention. These examples and illustrations are not to be construed in any way as limiting the scope of this invention.

EXAMPLES

EXAMPLE 1

To a 5-liter reaction flask fitted with a stirrer, Dean-Stark trap, condensor and nitrogen inlet; was charged 2000 g of a succinimide dispersant composition [prepared by reacting 1 mole of polyisobutenyl succinic anhydride, where the polyisobutenyl group has a number average molecular weight of about 950, with 0.9 mole of triethylenetetramine then diluting to about 50% actives with diluent oil to give a material with an AV=40.9 mg KOH/g]. To this mixture was added 352 g ethylene carbonate. The reaction mixture was stirred and heated at 150° C. under $N_2$ for 4 hours, then stripped for 30 minutes at 175°–180° C. and 2 mm Hg. Recovered 2020 g of prouct with AV=25.5.

EXAMPLE 2

To a 5-liter reaction flask was added 2000 g of a succinimide dispersant composition as described in Example 1 and 352 g ethylene carbonate. The mixture was stirred and heated at 150° C. under $N_2$ for 4 hours. The product was then cooled, diluted with 400 g diluent, and stripped to 200° C. and 10 mm Hg. Recovered 2048 g of product with AV=25.4 and containing 2.13% N.

EXAMPLE 3

To a 500-ml reaction flask was charged 100 g of a succinimide dispersant composition [prepared by reacting 1 mole of polyisobutenyl succinic anhydride, where the polyisobutenyl group has a number average molecular weight of about 950, with 0.87 mole of tetraethylenepentamine; then diluting to about 50% actives with diluent oil to give a material with an AV=46.3 mg KOH/g]. The succinimide was warmed to 150° C., 29.9 g ethylene carbonate was added, and the mixture stirred and heated at 150° C. under $N_2$ for 4 hours. The product was then cooled, diluted with 250 hydrocarbon thinner which is a mixture of aromatics, paraffins and naphthenes, and stripped to 175° C. and 13 mm Hg. Recovered 117.5 g of product having an AV=24.3 and containing 1.74% N.

EXAMPLE 4

To a 3-liter reaction flask was charged 1500 g of a succinimide dispersant composition [prepared by reacting 1 mole of polyisobutenyl succinic anhydride, where the polyisobutenyl group has a number average MW of about 950, with 0.5 mole of tetraethylenepentamine then diluting to about 50% actives with diluent oil and to give a material with an AV=27.5]. The succinimide was warmed to 170° C. and 171 g ethylene carbonate added over a period of about 5 minutes. The reaction mixture was stirred at 170° C. under $N_2$ for 4 hours to yield 1605 g of product with AV=15.5 and containing 1.40% N.

EXAMPLE 5

To a 3-liter reaction flask was charged 1700 g of the succinimide dispersant composition of Example 4. The succinimide was warmed to 170° C. under $N_2$ and 88.5 g ethylene carbonate was added. The reaction mixture was stirred and heated at 170° C. for 4 hours. Recovered 1702 g product having an AV=16.0 and containing 1.32% N.

EXAMPLE 6

To a 500-ml reaction flask was charged 100 g of the product of Example 5. The dispersant was warmed to 60° C. whereupon 6.2 g boric acid was added. The reaction mixture was stirred and heated at 160° under $N_2$ for 2 hours, then stripped to 175° C. and about 80 mm Hg. Recovered 101.6 g product having an AV=15.8 and containing 1.26% N and 1.01% B.

EXAMPLE 7

To a 500-ml reaction flask was charged 100 g of succinimide dispersant composition of Example 4 and 5.91 g propylene carbonate. The reaction mixture was stirred and heated under nitrogen at 150° for 4 hours. The product was then cooled, diluted with 350 thinner, and stripped to 175° C. and 10 mm Hg. Recovered 102.6 g of product with an AV=21.9 and containing 1.31% N.

EXAMPLE 8

To a 500-ml flask was charged 150 g succinimide dispersant composition of Example 4 and 150 ml xylenes. The reaction mixture was brought to reflux and 17.1 g ethylene carbonate, mixed with 20 ml xylenes at 64° C., was added. The mixture was refluxed under $N_2$ for 4 hours, then stripped to 170° C. and 50 mm Hg. Recovered 157.8 g product having an AV=23.5 and containing 1.46% N.

EXAMPLE 9

To a 500-ml reaction flask was charged 150 g succinimide dispersant composition of Example 4. The succinimide was warmed to 170° C. and 17.1 g ethylene carbonate was then added over a period of 65 minutes. The reaction mixture was stirred and heated at 170° C. under $N_2$ for another 3 hours. Recovered 161.6 g product having an AV=15.9 and containing 1.40% N.

EXAMPLE 10

To a 1-liter reaction flask was charged 500 g succinimide dispersant composition of Example 4. This material was then stripped to 170° C. and 5 mm Hg to remove 1.5 g entrained water. 56.8 g Ethylene carbonate was then added over a 2-minute period and the reaction mixture stirred and heated at 170° C. under $N_2$ for 4 hours. Recovered 535.7 g product having AV=14.2 and containing 1.36% N.

EXAMPLE 11

To a 5-liter reaction flask was charged 2800 g succinimide dispersant composition of Example 4 and 493 g ethylene carbonate. The reaction mixture was then stirred and heated at 150° C. under $N_2$ for 4 hours. The product was cooled, diluted with 600 ml 450 thinner and stripped to 210° C. and 10 mm Hg. Recovered 2952 g product having an AV=12.3 and containing 1.25% N.

EXAMPLE 12

To a 500-ml reaction vessel was charged 264 g of an approximately 50% solution of polyisobutenyl succinic anhydride in diluent oil (where the polyisobutenyl group has a number average molecular weight of about 950) and 11.8 g tetraethylenepentamine (a commercial product containing a mixture of polyamines). The reaction mixture was heated under nitrogen to 153° C. and stirred for one hour. 16.5 g Ethylene carbonate was then added and the heating and stirring continued for another 2 hours. Recovered 276 g of material having AV=21.9 and containing 1.48% N.

EXAMPLE 13

To a 250 ml 3 neck flask fitted with a stirrer, Dean-Stark trap, condensor and nitrogen inlet was charged 62 g ethylene diamine. While stirring at 60° C., 26.7 g of dodecenyl succinic anhydride (mw=266) was added slowly dropwise over 1 hr. The mixture was then refluxed at 118° C. for 30 minutes, afterwards the excess ethylene diamine was distilled out at 160° C. over 3 hours. To the mixture was added 8.8 g of ethylene carbonate (mw=88). The system was then heated at 160° C. for 3 hrs. Recovered 40.7 g of product with AV=40 and N=7%.

EXAMPLE 14

To a 250 ml 3 neck flask fitted with a stirrer, Dean-Stark trap, condensor and nitrogen inlet was charged 26.7 g of dodecenyl succinic anhydride (mw=266). After heating to 120° C., 9.5 g of tetraethylene pentaamine (mw=189) was added over 30 minutes. The mixture was heated and stirred at 170° C. for 3 hrs. To this mixture was added 23.1 g of ethylene carbonate (mw=88). This system was stirred at 170° C. for 3 hrs. Recovered 43.2 g of product with AV=73 and N=6.09%.

EXAMPLE 15

To a 250 ml 3 neck flask fitted with a stirrer, Dean-Stark trap, condensor and nitrogen inlet was charged 68 g of 37% oil solution of a polybutenyl succinic anhydride (average mw=430); 9.5 g of tetraethylene pentaamine (mw=189) was added over 30 minutes. The mixture was heated and stirred at 170° C. for 3 hrs. To this mixture was added 26.4 g of ethylene carbonate (mw=88). This system was stirred at 170° C. for 3 hrs. Recovered 90.5 g of product with AV=45 and N=3.8%.

EXAMPLE 16

To a 500 ml 3 neck flask fitted with a stirrer, Dean-Stark trap, condensor and nitrogen inlet was charged 250 g of a 50% oil solution of a polybutenyl succinic anhydride (average mw=1050). 17.9 g of Dow E-100 TM heavy polyamine (average mw=303 available from Dow Chemical Company, Midland, Mich.) was added over 30 minutes. The mixture was heated and stirred at 170° C. for 3 hrs. To this mixture was added 52 g ethylene carbonate. This system was stirred at 160° C. for 4 hrs. Recovered 296.5 g of product with AV=27.1 and N=1.9%.

EXAMPLE 17

To a 250 ml 3 neck flask fitted with a stirrer, Dean-Stark trap, condensor and nitrogen inlet was charged 140 g of a 50% oil solution of a polybutenyl succinic anhydride (average mw=1400). 4.75 g of tetraethylene pentaamine (mw=189) was added over 30 minutes. The mixture was heated and stirred at 170° C. for 3 hrs. To this mixture was added 13.2 g of ethylene carbonate (mw=88). This system was stirred at 170° C. for 3 hrs. Recovered 143.6 g of product with AV=13.3 and N=1.2%.

EXAMPLE 18

To a 250 ml 3 neck flask fitted with a stirrer, Dean-Stark trap, condensor and nitrogen inlet was charged 100 g of the succinimide dispersant composition of Example 4 and 13.2 g of 1,3-dioxan-2-one. The mixture was heated at 165° C. for 3 hrs. under nitrogen. After cooling the recovered product had an AV=18.1.

Similarly, other polyamino alkenyl or alkyl succinimides may be employed in place of the succinimides used in Examples 1-11 to produce modified succinimides useful in this invention. Examples of suitable succinimides include the reaction product of either polyisopropenyl succinic anhydride or polyisobutenyl succinic anhydride with bisaminopropylethylene diamine and the reaction product of a hydrogenated polyisobutenyl succinic anhydride with tetraethylene pentamine.

EXAMPLE 19

A 500 ml, 3-necked flask was charged with 123.3 g succinimide dispersant composition of Example 4 and 46 g pentaerythritol carbonate (spiro[1,3-oxa-2-cyclohexanone-5,5'-1',3'-oxa-2'-cyclohexanone]) which was prepared by reacting pentaerythritol with an excess of diethylcarbonate in the presence of catalytic amounts of potassium carbonate. The system was stirred and heated under nitrogen to 175° C. for 6½ hours to yield 138 g of a product having an AV=12.6.

EXAMPLE 20

A 500 ml, 3-necked flask was charged with 100 g succinimide dispersant composition of Example 4. The system is heated to 100° C. and 7.64 g of a mixture of 4-hydroxymethyl-1,3-dioxolan-2-one and 5-hydroxy-1,3-dioxan-2-one (which was prepared by reacting glycerol with an equivalent of diethylcarbonate in the presence of catalytic amounts of potassium carbonate without purifying the resulting product) was then added. The system was stirred and heated under nitrogen to 165° C. for 3 hours to yield 104.7 g of a product having % N=1.48.

Likewise, by following the procedures in the above examples, the following cyclic carbonates may be substituted for ethylene carbonate (1,3-dioxolan-2-one) to yield modified succinimides useful in this invention:

4-methyl-1,3-dioxolan-2-one; 4-hydroxymethyl-1,3-dioxolan-2-one; 4,5-dimetyl-1,3-dioxolan-2-one; 4-ethyl-1,3-dioxolan-2-one; 4-methyl5-ethyl-1,3-dioxolan-2-one; 4,4-dimethyl-1,3-dioxolan-2-one; 4-n-propyl-1,3-dioxolan-2-one; 4,4-diethyl-1,3-dioxolan-2-one; 1,3-dioxan-2-one; 4,4-dimethyl-1,3-dioxan-2-one; 5,5-dimethyl-1,3-dioxan-2-one; 5-methyl-1,3-dioxan-2-one; 4-methyl-1,3-dioxan-2-one; 5-hydroxymethyl-1,3-dioxan-2-one; 5,5-diethyl-1,3-dioxan-2-one; 5-methyl-5-npropyl-1,3-dioxan-2-one; 4,6-dimethyl-1,3-dioxan-2-one; 4,4,6-trimethyl-1,3-dioxan-2-one and spiro[1,3-oxa-2-cyclohexanon-5,5'-1',3'-oxa-2'-cyclohexanone].

EXAMPLE 21

A linear polyethylene carbonate was prepared according to U.S. Pat. No. 3,248,414. A stirred steel autoclave was charged with 12.4 g ethylene glycol, 274 g ethylene carbonate, and 0.4 g potassiium carbonate. The temperature was raised to 200° C. and held there for 24 hours. The pressure in the vessel rose from 155 psi to 1300 psi and was constant at 1300 psi for at least the last 5 hours of the reaction. The reactor temperature was lowered to 115°-120° C. and the reaction gases were vented. The product was then stripped under vacuum to 165°-170° C. to remove excess ethylene carbonate. Recovered 158.9 g product haivng an hydroxyl number of 157 and containing 14.9 weight percent $CO_2$.

EXAMPLE 22

A 500 ml, 3-necked flask was charged with 80 g monosuccinimide disperesant composition of Example 3 and 20.8 g. polycarbonate of Example 21. The mixture was stirred and heated under nitrogen for 4 hours at 160° C., whereupon the AV of the mixture dropped from 39.8 to 33.8 mg KOH/g. The mixture was then heated at 180° C. for another 5 hours, whereupon the AV dropped to 28.7 mg KOH/g The mixture was finally heated at 200° C. for 2½ hours to give a product having an AV=28.4 mg KOH/g and showing no unreacted carbonate by infrared spectroscopy.

EXAMPLE 23

A 500 ml, 3-necked flask was charged with 100 g bissuccinimide dispersant composition of Example 4, 11.8 g polycarbonate of Example 21, and 180 ml p-dioxane. The mixture was refluxed for 1 hour, then the p-dioxane was removed by distillation. The remaining reaction mixture was warmed to 180° C. under nitrogen for 5 hours, then at 220° C. for 5½ hours. Recovered a product having an AV=17.6 mg KOH/g.

EXAMPLE 24

To a 250 ml, 3-necked flask was charged 46.4 g of a bissuccinimide dispersant composition of Example 4 and 1.3 g of a polycarbonate resin having the generic formula $(C_6H_4-C(CH_3)_2-C_6H_4OCO_2)_n$ and an MW=20,000-25,000 (available from Aldrich Chemical Co., Milwaukee, Wis., as Aldrich No. 78,162-5). The mixture was heated under nitrogen to 150° C. for 5 hours. Recovered 0.7 g unreacted polycarbonate resin. The recovered product had an AV=25.3 mg KOH/g.

EXAMPLE 25

To a 250 ml, 3-necked flask was charged 46.4 g of the bissuccinimide dispersant composition of Example 4 and 5.1 g polycarbonate resin as described in Example 24. The mixture was heated under nitrogen to 150°-160° C. for 3½ hours, then to 180°-190° C. for another 1½ hours. Recovered 3.15 g unreacted polycarbonate resin. The product contained 1.42% N and had an AV=16.4 mg KOH/g.

EXAMPLE 26

To a 500 ml, 3-necked flask was added 5.1 g of the polycarbonate resin described in Example 24 and 100 g p-dioxane. The solvent was refluxed until all the resin had dissolved. 46.4 g of the bissuccinimide dispersant composition of Example 4 was then added and refluxing continued for another 21 hours. The reaction mixtures was then stripped to remove dioxane and heated to 180°-190° C. under $N_2$ for 3 hours. The product contained 1.32% N and had an AV=10.0 mg KOH/g.

EXAMPLE 27

To a 3-liter, 3-necked flask was charged 1700 g of a bissuccinimide (prepared by reacting 2 moles of polyisobutenyl succinic anhydride where the polyisobutenyl group has a number average MW=950, with 1 mole of tetraethylene pentamine then diluting to about 50% actives with diluent oil to give a material with an AV=27.5). The bissuccinimide was brought to 170° C. under a nitrogen atmosphere and 88.5 g ethylene carbonate was added over a period of about three minutes. The mixture was stirred at 170° C. for 4 hours. Recovered 1762 g product containing 1.32% nitrogen and having an AV=15.7 mg KOH/g.

EXAMPLE 28

To a 500 ml, 3-necked flask was charged 132.6 g of the product of Example 27 and 76.5 g of an approximately 50% oil solution of polyisobutenyl succinic anhydride (MW=1050). The mixture was stirred and heated under nitrogen at 160° C. for 2 hours. Recovered 209.2 g product containing 0.85% N and having an AV=8.4 mg KOH/g.

EXAMPLE 29

To a 3-liter, 3-necked flask was charged 1500 g of a bissuccinimide dispersant composition of Example 27. The succinimide was warmed to 170° C. under a nitrogen atmosphere and 171 g ethylene carbonate was added over a period of 8 minutes. The mixture was stirred at 170° C. for 4 hours. Recovered 1605 g product containing 1.41% N and having an AV=15.5 mg KOH/g.

EXAMPLE 30

To a 500 ml, 3-necked flask was charged 197.2 g of the product of Example 29 and 40.8 g of an approximately 50% oil solution of polyisobutylene succinic anhydride (MW=1050). The mixture was warmed to 170° C. and stirred for 3 hours under a nitrogen atmosphere. Recovered 240 g product containing 1.17% N and having an AV=11.5 mg KOH/g.

EXAMPLE 31

To a 500 ml, 3-necked flask was charged 263.2 g of the dispersant of Example 29 and 76.5 g of an approximately 50% oil solution of polyisobutenyl succinic anhydride (MW=1050). The mixture was stirred and heated under nitrogen at 160° C. for 2 hours. Recovered 339 g product having an AV=10.8 mg KOH/g.

EXAMPLE 32

To a 500 ml, 3-necked flask was charged 197.2 g of the product of Example 29 and 81.6 g of an approximately 50% oil solution of polyisobutenyl succinic anhydride (MW=1050). The mixture was stirred and heated under nitrogen at 170° C. for 3 hours. Recovered 279.2 g of product containing 0.98% N and having an AV=10.1 mg KOH/g.

EXAMPLE 33

To a 500 ml, 3-necked flask was charged 150 g of a bissuccinimide dispersant composition of Example 27. This succinimide was warmed to 150° C. under nitrogen and 25.6 g ethylene carbonate was added. The mixture was stirred and heated at 150° C. for 4 hours; 150 ml xylenes was then added and the product stripped to 170° C. and 50 mm Hg for 30 minutes. Recovered 165.1 g product containing 1.38% N and having an AV=14.4 mg KOH/g.

EXAMPLE 34

To a 500 ml, 3-necked flask was charged 126.8 g of the product of Example 33 and 76.5 g of an approximately 50% oil solution of polyisobutenyl succinic anhydride (MW=1050). The mixture was placed under nitrogen and heated and stirred at 160° C. for 2 hours. Recovered 203.3 g product containing 0.86% N and having an AV=7.7 mg KOH/g.

EXAMPLE 35

To a 500 ml, 3-necked flask was charged 100 g of bissuccinimide dispersant composition of Example 27. This succinimide was warmed to 160° C. under nitrogen and 6.7 g propylene carbonate added. The mixture was heated and stirred at 160° C. for 4 hours. 67.3 g polyisobutenylsuccinic anhydride (MW=1050) was then added and the mixture stirred at 160° C. for an additional 2 hours. Recovered 172.6 g product containing 0.87% N and having an AV=7.2 mg KOH/g.

EXAMPLE 36

To a 3-liter, 3-necked flask was charged 1500 g of an approximately 43% oil solution of a monosuccinimide (prepared by reacting 1 mole polyisobutenyl succinic anhydride where the polyisobutenyl group has a number average MW=950 with 0.87 mole TEPA, and containing 2.06% N and having an AV=45.1). This succinimide was warmed to 170° C. under nitrogen and 149.6 g ethylene carbonate was added. The mixture was stirred at 170° C. for 2 hours. Recovered 1551 g product containing 1.97% N and having AV=26.0 mg KOH/g.

EXAMPLE 37

To a 500 ml, 3-necked flask was charged 177.7 g of the product of Example 36 and 204.0 g of an approximately 50% oil solution of polyisobutenylsuccinic anhydride (MW=1050). The mixture was warmed to 160° C. under nitrogen and stirred for 2 hours. Recovered 381.6 g product containing 0.82% N and having an AV=10.3 mg KOH/g.

EXAMPLE 38

To a 500 ml, 3-necked flask was charged 100 g of the monosuccinimide dispersant composition of Example 36. This succinimide was warmed to 160° C. under nitrogen and 21.1 g ethylene carbonate added. The mixture was stirred at 160° C. for 4 hours, whereupon 122.4 g of an approximately 50% oil solution of polyisobutenylsuccinic anhydride (MW=1050) was added. Heating was continued for another 2 hours. Recovered 232 g product containing 0.92% N and having an AV=10.5 mg KOH/g.

EXAMPLE 39

To a 500 ml, 3-necked flask equipped with a nitrogen inlet, mechanical stirrer and addition funnel was charged 150 g of the monosuccinimide dispersant composition of Example 3 and 20.9 g of diethylcarbonate. The reaction system was heated to 160° C. for 6 hours. The temperature was raised to 175° C. and then the reaction system was stripped under vacuum to remove volatiles and some diluent oil. 150.5 g of the product was recovered having an AV=42.2. Infrared shows carbamate and succinimide bands at from 1710 cm$^{-1}$ to 1690 cm$^{-1}$.

EXAMPLE 40

To a 100 ml flask under nitrogen equipped with a stirrer and an addition funnel was charged 5 g of the bissuccinimide disperesant composition of Example 27. Afterwards approximately 1.5 g of methyl chloroformate was slowly added dropwise over 1 hour to the reaction system at a temperature of from 25° C. to 30° C. at this time, infrared analysis shows the presence of unreacted chloroformate. The reaction was exothermic and the system was heated from 45° to 75° C. over 1 hour and then allowed to cool and 250 hydrocarbon thinner, which is a mixture of aromatics, paraffins and naphthenes, was added The organic solution was washed with brine to remove hydrogen chloride and unreacted chloroformate and then stripped to yield methyl carbamate derivatives of the bissuccinimide having an AV=5.42.

EXAMPLE 41

To a 3-liter, 3-necked flask is charged 1,250 g of the monosuccinimide dispersant composition of Example 36. Afterwards, 276 g of tetradecyl chloroformate (prepared by reacting 1-tetradecanol with phosgene) is slowly added to the reaction system at a temperature from 20°-25° C. The reaction system is stirred at this temperature for 2 hours at which time the reaction solution is added to 250 hydrocarbon thinner which is a mixture of aromatics, paraffins, and naphthenes. The organic solution is washed with brine and then stripped to remove volatiles to yield a dispersant product containing tetradecyl carbamate functionalities.

EXAMPLE 42

To a 5-liter, 3-necked flask is charged 1,250 g of the monosuccinimide dispersant composition of Example 36. Afterwards, 1,440 g of eicosyl chloroformate (prepared by reacting 1-eicosanol with phosgene) is slowly added to the reaction system at a temperature from 20°-25° C. The reaction system is stirred at this temperature for 3 hours at which time the reaction solution is added to 250 hydrocarbon thinner which is a mixture of aromatics, paraffins and naphthenes. The organic solution is washed with brine and then stripped to remove volatiles to yield a dispersant product containing eicosyl carbamate functionalities.

EXAMPLE 43

Preparation of Ethylene Glycol Mono-Trichloroacetate

To a 3-neck flask equipped with a nitrogen inlet tube, a mechanical stirrer and a dean stark trap was added 37.2 g of ethylene glycol (0.6 moles) and 49.0 g of trichloroacetic acid (0.3 moles). The mixture was heated at 150° C. for 3.5 hours. Water distills out of the reaction mixture and is collected in the Dean-Stark trap. After cooling, the crude mixture was dissolved in 150 ml of methylene chloride and was washed three times with 150 ml of ice water. The organic phase was dried over anhydrous sodium sulfate, filtered and the solvent was removed under vacuum to give the mono-trichloroacetate as the major product.

A sample of ethylene glycol mono-trichloroacetate, prepared similarly to the procedure outlined above, was placed on TLC (thin layer chromatography). TLC shows the mono-trichloroacetate having a $R_f$=0.33 and the bis-trichloroacetate having a $R_f$=0.67 using 1/5 ethyl acetate/petroleum ether as development solvent and a dichromate stain for visualization.

A sample of mono-trichloroacetate was purified by silica gel chromatography. The crude material (90.8 g) was placed on a column packed with 484 g of silica gel and eluted with 5% ethyl acetate/hexane. The mono-trichloroacetate has an $R_f$=0.25 in this solvent system and 58.2 g was obtained as single spot material. IR shows hydroxy at 3400 cm$^{-1}$ and carbonyl at 1765 cm$^{-1}$. NMR (CDCl$_3$) shows 1H(—OH) at delta 3.35, 2H(—CH$_2$—O) at delta 4.0 and 2H(C—O—CH$_2$—C) at delta 4.55. The bis-trichloroacetate was also obtained pure by silica gel chromatography. IR shows carbonyl at 1770 cm$^{-1}$ and no hydroxy. NRR (CDCl$_3$) shows only 4H(—CH$_2$—O) at delta 4.75.

EXAMPLE 44

Preparation of Chloroformate of Ethylene Glycol Mono-Trichloroacetate

Ethylene glycol mono-trichloroacetate, 14.5 g, 0.07 moles, was dissolved in 100 ml of toluene and excess phosgene was carefully passed through the solution for several hours. (The reaction was performed in a well ventilated hood and a KOH scrubber was used to destroy unreacted phosgene and HCl gas). The reaction was monitored by TLC until all of the starting material was gone. After the reaction was completed, nitrogen was bubbled through the solution to remove any unreacted phosgene. The toluene solution containing the chloroformate can be used in subsequent reactions.

A sample of the chloroformate of ethylene glycol mono-trichloroacetate was prepared similarly to the procedure outlined above and placed on a TLC. The chloroformate appears as a new single spot on TLC at $R_f=0.6$ using ⅓ ethyl acetate/hexane as solvent (dichromate visualization). A portion of a chloroformate/toluene solution was stripped and IR shows carbonyl (trichloroacetate and chloroformate) at 1770 cm$^{-1}$ and no hydroxyl group. NMR shows a broad 4H singlet at delta 4.7.

EXAMPLE 45

Preparation of a Hydroxy Ethyl Carbamate Modified Succinimide. Reaction of Protected Chloroformate with Bissuccinimide (a) The chloroformate of ethylene glycol monotrichloroacetate, 3.9 g (0.0144 moles) was dissolved in 20 ml toluene. 20.3 g of a bissuccinimide dispersant composition (prepared by reacting 1 mole of polyisobutenyl succinic anhydride, where the polyisobutenyl group has a number average MW of about 950, with 0.5 mole of tetraethylene pentaamine then diluting to about 50% actives in diluent oil to give a material with an AV=29.7 and a nitrogen content of 1.51%) was dissolved in 25 ml of toluene. Both solutions were cooled to below 0° C. (approximately −2° C.) using a salt ice-water bath. The solutions were poured together into a 500 ml flask equipped with a mechanical stirrer and drying tube attached. The reaction solution was mixed with strong stirring and kept below 0° C. for 40 minutes and then allowed to warm to room temperature.

(b) After stirring at room temperature for several hours, about 65 mls of the reaction solution was added to 130 mls hexane and 65 mls 1N NaOH in a separatory funnel in order to remove the trichloroacetate group. The mixture was intermittantly shaken for 30 minutes. After phase separation, the organic layer was washed several times with brine, dried over anhydrous magnesium sulfate, filtered and stripped to yield the title product having an AV=18.4. The infrared spectrum of this product contains a hydroxy band at 3400 cm$^{-1}$ and succinimide and carbamate bands at 1710 cm$^{-1}$ to 1690 cm$^{-1}$.

(c) Alternatively, the trichloroacetyl group may be removed as follows:

A 5 ml sample from (a) above was added to 10 ml of hexane and about 0.25 ml of di-n-butyl amine. Afterwards, the solution was stirred in a 50 ml flask at room temperature overnight and then heated to 40° C. for 40 minutes, followed by 2 additional hours at room temperature. An aliquot was then removed and stripped. Infrared analysis of this sample indicated that the trichloroacetyl group had been removed. The reaction mixture was then washed several times with brine and then stripped under vacuum to yield a product identical to that produced in (b) above.

EXAMPLE 46

(a) The chloroformate of ethylene glycol mono-trichloroacetate, 1.7 g, was dissolved in 25 ml toluene. 3.8 g of a bissuccinimide (prepared by reacting 1 mole of dodecenyl succinic anhydride with 0.5 mole of diethylene triamine to yield the bissuccinimide) was dissolved in 35 ml of toluene. Both solutions were cooled to below 0° C. (approximately −2° C.) using a salt ice-water bath. The solutions were poured together into a flask equipped with a mechanical stirrer and drying tube. The reaction solution was mixed with strong stirring and kept below 0° C. for 40 minutes and then allowed to warm to room temperature. After reaction completion, the reaction solution was stripped under vacuum to yield a crude product. This product was purified by column chromatography using 80 g silica gel and 1:1 ethyl acetate/hexane as the eluting solvent to recover 3.7 g of the trichloroacetyl ethyl carbamate of the bissuccinimide. Infrared analysis shows a trichloroacetyl band at 1770 cm$^{-1}$ and succinimide and carbamate bands at 1710–1690 cm$^{-1}$.

(b) 1 g of the product of (a) above was added to 20 ml hexane and 10 ml 1N NaOH in order to remove the trichloroacetate group. The mixture was intermittantly mixed. After phase separation, the organic layer was washed several times with brine, dried over anhydrous magnesium sulfate, filtered and stripped to yield the title compound.

EXAMPLE 47

Preparation of Glycerol Di-(trichloroacetate)

To a 3-neck flask equipped with a nitrogen inlet tube, a mechanical stirrer and a Dean-Stark trap is added 92 g of glycerol and 326.8 g of trichloroacetic acid. The mixture is heated at 150° C. for 3.5 hours. Water distills out of the reaction mixture and is collected in the Dean-Stark trap. After cooling, the crude mixture is dissolved in 150 ml of methylene chloride and is washed three times with 150 ml of ice water. The organic phase is dried over anhydrous sodium sulfate, filtered and the solvent is removed under vacuum to give the di(trichloroacetate) of glycerol which is purified by column chromatography using silica gel.

EXAMPLE 48

Preparation of Chloroformate of Glycerol Di-(trichloroacetate)

Glycerol di-(trichloroacetate) 36.1 g, is dissolved in 200 ml of toluene and excess phosgene is carefully passed through the solution for several hours. (The reaction is preformed in a well ventilated hood and a KOH scrubber is used to destroy unreacted phosgene and HCl gas.) The reaction is monitored by TLC until all of the starting material is gone. After reaction completion, nitrogen is bubbled through the solution to remove any unreacted phosgene to yield a toluene solution containing the title product.

EXAMPLE 49

The chloroformate of glycerol di(trichloroacetate), 42.3 g, is dissolved in 200 ml toluene. 300 g of a monosuccinimide dispersant composition (prepared by reacting 1 mole of polyisobutenyl succinic anhydride, where the polyisobutenyl group has a number average molecular weight of about 950, with 0.87 mole of tetraethylene pentaamine then diluting to about 50% actives in diluent oil) is dissolved in 200 ml toluene. Both solutions are cooled to below 0° C. (approximately −2° C.) using a salt ince-water bath. The solutions are poured together into a 2 l flask equipped with a mechanical stirrer and a drying tube. The reaction solution is mixed with strong stirring and kept below 0° C. for 40 minutes and then is allowed to warm to room temperature. After stirring at room temperature for several hours, about 65 mls of the reaction mixture is added to 130 mls hexane and 65 mls 1N NaOH in a separatory funnel in order to remove the trichloroacetate group. The mixture is intermittantly shaked for 30 minutes. After phase separation, the organic layer is washed several times with brine, is dried over anhydrous magnesium sulfate, is filtered and stripped to yield the dihydroxypropylcarbamate derivatives of the monosuccinimide.

EXAMPLE 50

To a 3-neck flask equpped with a nitrogen inlet tube, a mechanical stirrer and a Dean-Stark trap is added 36 g of polyethylene glycol (average MW=600—available from Aldrich Chemical Co., Milwaukee, Wis. as Aldrich 20,240-1) and 4.9 g of trichloroacetic acid. The mixture is heated at 150° C. for 3.5 hours. Water distills out of the reaction mixture and is collected in the Dean-Stark trap. After cooling, the crude mixture is dissolved in 150 ml of methylene chloride and is washed three times with 150 ml of ice-water. The organic phase is dried over anhydrous sodium sulfate, filtered and the solvent is removed to give polyethylene glycol monotrichloroacetate which is purified by column chromatography using silica gel.

By following the procedures outlined in Examples 44, 45, 46, 48 and 49, the chloroformate of the polyethylene glycol monotrichloroacetate is prepared which then is reacted with a succinimide of this invention and then is then deprotected to yield a succinimide wherein one or more of the basic nitrogens has been converted to a hydroxy polyoxyethylene carbamate.

By following the procedures of Examples 43–50, the following alkylene glycols may be substituted for ethylene glycol:

1,3-propylene glycol; 1,3-butanediol; 1,4-butanediol; 1,4-pentanediol; 1,5-pentanediol; 1,6-hexanediol; 1,9-nonanediol; 1,10-decanediol; 1,2-octadecanediol; 1,2-hexadecanediol; pentaerythritol and glucose.

EXAMPLE 51

Formulated oils containing different modified succinimides of the invention were tested in a Sequence V-D Test method (according to candidate test for ASTM). This procedure utilizes a Ford 2.3-liter, four-cylinder Pinto engine. The test method simulates a type of severe field test service characterized by a combination of low speed, low temperature "stop and go" city driving and moderate turnprke operation. The effectiveness of the additives in the oil is measured in terms of the protection against sludge and varnish deposits on a 0 to 10 scale with 0 being black and 10 indicating no varnish or sludge deposits. The result are indicated in Table II.

The comparisons were made in a formulated oil containing a succinimide dispersant, 20 mmoles of an overbased calcium phenate, 30 mmoles as an overbased calcium sulfonate, 0.16% zinc as primary alkyl zinc dithiophosphate, and a nondispersant ethylene-propylene copolymer VI improver to give an SAE 10W40 oil.

TABLE II

| Formulation Contained 6% Succinimide of Example | Average[4] Varnish | Average[4] Sludge |
| --- | --- | --- |
| Starting succinimide of Example 4 | 4.8 | 9.5 |
| Example 4 | 5.6 | 9.5 |
| Example 5 | 6.8 | 9.5 |
| Example 11 | 7.4 | 9.6 |

[4]mean of 2 runs

EXAMPLE 52

In some cases, succinimides which give superior results in spark-ignition engines give less than desirable performance in diesel engines. However, the modified succinimides of the instant invention give diesel engine dispersancy performance comparable to succinimides as reported below. The compositions of this invention were tested in a Caterpillar 1-G2 test in which a single-cylinder diesel engine having a $5\frac{1}{8}''$ bore by $6\frac{1}{2}''$ stroke is operated under the following conditions: timing, degrees BTDC, 8; brake mean effective pressure, psi 141; brake horsepower 42; Btu's per minute 5850; speed 1800 RPM; air boost, 53" Hg absolute, air temperature in, 255° F.; water temperature out, 190° F.; and sulfur in fuel, 0.4%. At the end of each 12 hours of operation, sufficient oil is drained from the crankcase to allow addition of 1 quart of new oil. In the test on the lubricating oil compositions of this invention, the 1-G2 test is run for 60 hours. At the end of the noted time period, the engine is dismantled and rated for cleanliness. These results are reported below. Lower values represent cleaner engines.

The base oil used in these tests is a midContinent base stock SAE 30 oil containing 18 mmols/kg of a zinc dihydrocarbyl dithiophosphate, 36 mmols/kg of an overbased calcium phenate, and the amount noted in the table of dispersant.

Test Results - 1-G2 Caterpillar Test (60 Hours)

| 6% Dispersant of Example | Top Groove fill, % | Weighted Total Demerits (WTD) |
| --- | --- | --- |
| Starting Succinimide of Example 1 | 63 ± 15[6] | 259 ± 51[6] |
| Example 1 | 67 | 241 |
| Example 1 | 75 | 289 |

[6]average of 7 runs.

What is claimed is:

1. A product prepared by the process which comprises reacting (a) a polyamino alkenyl or alkyl succinimide wherein one or more of the nitrogens of the polyamino moiety is substituted with a hydroxyhydrocarbyl oxycarbonyl wherein the hydroxyhydrocarbyl group of said hydroxyhydrocarbyl oxycarbonyl contains from 2 to 20 carbon atoms and 1 to 6 hydroxy groups with the proviso that there is no hydroxy substitution on the hydrocarbyl carbon atom attaching the hydroxyhydrocarbyl group to the oxy atom of the oxycarbonyl group and with the further proviso that when more than one hydroxy group is contained in the hydroxyhydrocarbyl group, no more than one hydroxy group is attached to the same carbon atom and the number of carbon atoms in the hydroxyhydrocarbyl group is minimally one greater than the number of hydroxy groups, with (b) an alkenyl or alkyl succinic anhydride of the formula:

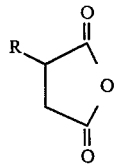

wherein R is alkenyl or alkyl of from 10 to 300 carbon atoms and wherein the process employs from about 0.1 to 1.5 equivalents of the alkenyl or alkyl succinic anhydride per equivalent of the modified polyamino alkenyl or alkyl succinimide of (a) above.

2. A product prepared by the process defined in claim 1 wherein the alkenyl or alkyl group of said polyamino alkenyl or alkyl succinimide contains from 10 to 300 carbon atoms.

3. A product prepared by the process defined in claim 1 wherein the alkenyl or alkyl group of said polyamino alkenyl or alkyl succinimide contains from 20 to 100 carbon atoms.

4. A product prepared by the process defined in claim 3 wherein the hydroxyhydrocarbyl group of said hydroxyhydrocarbyl oxycarbonyl contains from 1 to 3 hydroxy groups.

5. A product prepared by the process defined in claim 4 wherein the hydroxyhydrocarbyl group of said hydroxyhydrocarbyl oxycarbonyl contains 1 hydroxy group.

6. A product prepared by the process defined in claim 4 wherein the hydroxyhydrocarbyl group of said hydroxyhydrocarbyl oxycarbonyl is selected from the group consisting of 2-hydroxyethyl, 3-hydroxypropyl, hydroxyisopropyl, 4-hydroxybutyl, 6-hydroxyhexyl and 2,3-dihydroxypropyl.

7. A product prepared by the process defined in claim 6 wherein said hydroxyhydrocarbyl oxycarbonyl is 2-hydroxyethyl oxycarbonyl.

8. A product prepared by the process which comprises reacting (a) a polyamino alkenyl or alkyl succinimide wherein one or more of the nitrogens of the polyamino moiety is substituted with a hydroxypoly(oxyalkylene)oxycarbonyl, with (b) an alkenyl or alkyl succinic anhydride of the formula:

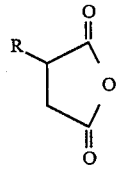

wherein R is alkenyl or alkyl of from 10 to 300 carbon atoms and wherein the process employs from about 0.1 to 1.5 equivalents of the alkenyl or alkyl succinic anhydride per equivalent of the modified polyamino alkenyl or alkyl succinimide of (a) above.

9. A product prepared by the process defined in claim 8 wherein the alkenyl or alkyl group of said polyamino alkenyl or alkyl succinimide contains from 10 to 300 carbon atoms.

10. A product prepared by the process defined in claim 9 wherein the alkenyl or alkyl group of said polyamino alkenyl or alkyl succinimide contains from 20 to 100 carbon atoms.

11. A product prepared by the process defined in claim 10 wherein the poly(oxyalkylene) group of said hydroxy poly(oxyalkylene)oxycarbonyl contains from 2 to 30 $C_2$–$C_5$ oxyalkylene units.

12. A product prepared by the process defined in claim 11 wherein the poly(oxyalkylene) group of said hydroxy poly(oxyalkylene)oxycarbonyl contains from 2 to 20 $C_2$–$C_5$ oxyalkylene units.

13. A product prepared by the process which comprises reacting (a) a polyamino alkenyl or alkyl succinimide of the formula:

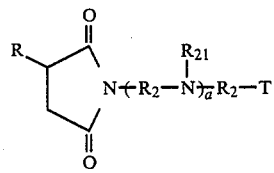

wherein R is alkenyl or alkyl of from 10 to 300 carbon atoms; $R_2$ is alkylene of from 2 to 10 carbon atoms; $R_{21}$ is selected from the group consisting of hydrogen, lower alkyl of from 1 to 6 carbon atoms, lower hydroxy alkyl of from 1 to 6 carbon atoms,

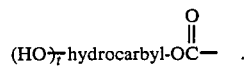

wherein t is an integer from 1 to 6, and hydrocarbyl is a hydrocarbyl group of from 2 to 20 carbon atoms with the proviso that there is no hydroxy substitution on the hydrocarbyl carbon atom attaching the $(HO)_t$ hydrocarbyl group to the oxy atom of the

group and with the further proviso that when t is greater than one, the hydroxy groups are not attached to the same carbon atom and the number of carbon atoms in the $(HO)_t$ hydrocarbyl group is minimally equal to t+1, and

wherein alkylene-O is a $C_2$–$C_5$ oxyalkylene and s is an integer from 2 to 20; a is an integer of from 0 to 10; and T is selected from the group consisting of —$NH_2$,

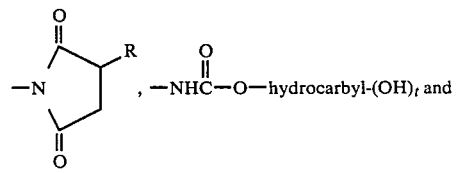

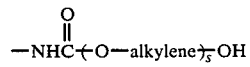

wherein R, hydrocarbyl, alkylene, s and t are as defined above; with still the further proviso that if T is —$NH_2$ or

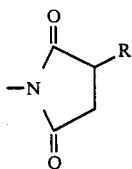

then a is not zero and at least one of $R_{21}$ is either

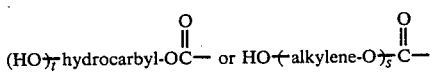

with (b) an alkenyl or alkyl succinic anhydride of the formula:

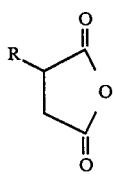

wherein R is alkenyl or alkyl of from 10 to 300 carbon atoms and wherein the process employs from about 0.1 to 1.5 equivalents of the alkenyl or alkyl succinic anhydride per equivalent of the modified polyamino alkenyl or alkyl succinimide of (a) above.

14. A product prepared by the process defined in claim 13 wherein R is alkenyl or alkyl of from 20 to 100 carbon atoms.

15. A product prepared by the process defined in claim 14 wherein $R_2$ is alkylene of from 2 to 6 carbon atoms.

16. A product prepared by the process defined in claim 15 wherein a is an integer of from 1 to 6.

17. A product prepared by the process defined in claim 15 wherein $R_{21}$ is

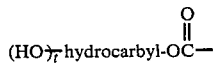

and t is 1.

18. A product prepared by the process defined in claim 17 wherein T is selected from the group consisting of:

or

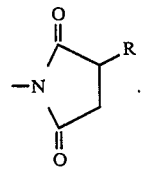

19. A product prepared by the process defined in claim 18 wherein t is 1.

20. A product prepared by the process defined in claim 19 wherein $R_{21}$ is

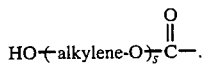

21. A product prepared by the process which comprises (a) contacting at a temperature sufficient to cause reaction a polyamino alkenyl or alkyl succinimide having at least one primary or secondary amine with a cyclic carbonate wherein the molar charge of the cyclic carbonate to the basic nitrogen of the polyamino alkenyl or alkyl succinimide is from about 0.2:1 to about 10:1; (b) reacting the product of (a) above with an alkenyl or alkyl succinic anhydride of the formula:

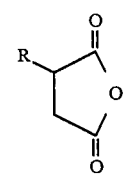

wherein R is alkenyl or alkyl of from 10 to 300 carbon atoms and wherein the process employs from about 0.1 to 1.5 equivalents of the alkenyl or alkyl succinic anhydride per equivalent of the modified polyamino alkenyl or alkyl succinimide of (a) above.

22. A product prepared by the process defined in claim 20 wherein the cyclic carbonate is selected from the group consisting of:

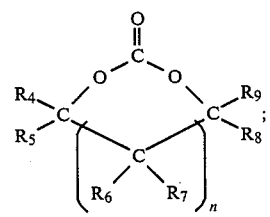 (1)

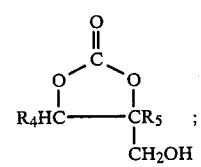 (2)

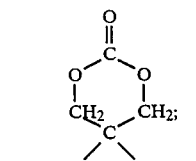 (3)

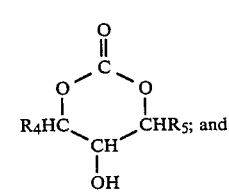 (4)

-continued

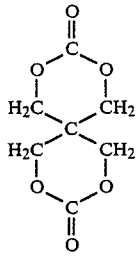 (5)

wherein $R_4$, $R_5$, $R_6$, $R_7$, $R_8$ and $R_9$ are independently selected from hydrogen or alkyl of from 1 to 2 carbon atoms; $R_{10}$ is hydroxy or hydrogen; and n is an integer from 0 to 1.

23. A product prepared by the process defined in claim 22 wherein the cyclic carbonate is

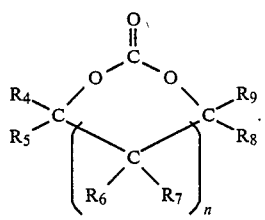

24. A product prepared by the process defined in claim 23 wherein n is zero and $R_4$, $R_5$, $R_8$ are hydrogen and $R_9$ is hydrogen or methyl.

25. A product prepared by the process defined in claim 24 wherein the cyclic carbonate is ethylene carbonate.

26. A product prepared by the process defined in claim 25 wherein the cyclic carbonate is propylene carbonate.

27. A product prepared by the process defined in claim 21 wherein the molar charge of the cyclic carbonate to the basic nitrogens of the alkenyl or alkyl succinimide is from about 0.5:1 to about 5:1.

28. A product prepared by the process defined in claim 27 wherein the molar charge of the cyclic carbonate to the basic nitrogens of the alkenyl or alkyl succinimide is fom about 1:1 to 3:1.

29. A product prepared by the process defined in claim 28 wherein the molar charge of the cyclic carbonate to the basic nitrogens of the alkenyl or alkyl succinimide is approximately 2:1.

30. A product prepared by the process which comprises (a) contacting at a temperature sufficient to cause reaction a polyamino alkenyl or alkyl succinimide of the formula II:

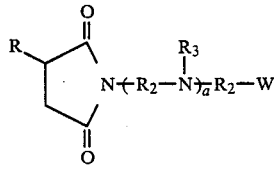 II wherein R is an alkenyl or alkyl group containing from about 10 to 300 carbon atoms; $R_2$ is alkylene of from 2 to 10 carbon atoms; $R_3$ is hydrogen or lower alkyl of from 1 to 6 carbon atoms; a is an integer from 0 to 10; and W is —$NH_2$ or represents a group:

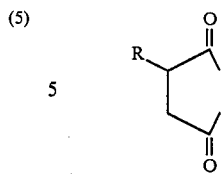

wherein R is an alkenyl or alkyl group containing from about 10 to 300 carbon atoms with the proviso that if W is

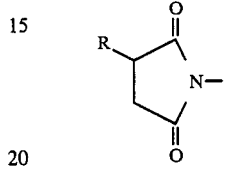

than a is not zero and at least one of $R_3$ is hydrogen; with a cyclic carbonate wherein the molar charge of the cyclic carbonate to the basic nitrogen of the alkenyl or alkyl succinimide is from about 0.2:1 to about 10:1, (b) reacting the product of (a) an alkenyl or alkyl succinic anhydride of the formula:

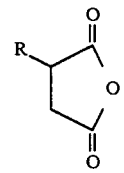

wherein R is alkenyl or alkyl of from 10 to 300 carbon atoms and wherein the process employs from about 0.1 to 1.5 equivalents of the alkenyl or alkyl succinic anhydride per equivalent of the modified polyamino alkenyl or alkyl succinimide of (a) above.

31. A product prepared by the process defined in claim 30 wherein R is an alkenyl or alkyl group of from 12 to 100 carbon atoms.

32. A product prepared by the process defined in claim 31 wherein $R_2$ is alkylene of from 2 to 6 carbon atoms, a is an integer from 1 to 6 and $R_3$ is hydrogen.

33. A product prepared by the process defined in claim 32 wherein the cyclic carbonate is selected from the group consisting of:

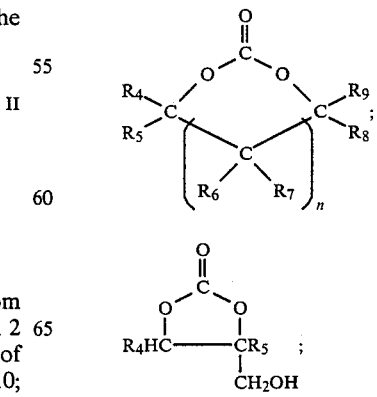

-continued

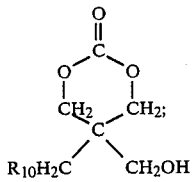

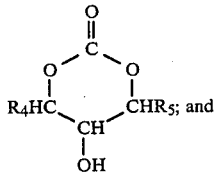

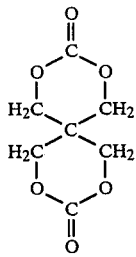

wherein $R_4$, $R_5$, $R_6$, $R_7$, $R_8$ and $R_9$ are independently selected from hydrogen or alkyl of 1 to 2 carbon atoms; $R_{10}$ is ether hydrogen or hydroxy; and n is an integer from 0 to 1.

34. A product prepared by the process defined in claim 33 wherein the cyclic carbonate is

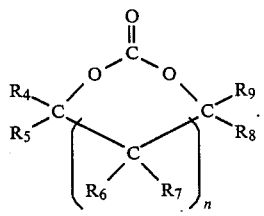

35. A product prepared by the process defined in claim 34 wherein n is zero and $R_4$, $R_5$ and $R_8$ are hydrogen and $R_9$ is hydrogen or methyl.

36. A product prepared by the process defined in claim 35 wherein the molar charge of the cyclic carbonate to the basic nitrogens of the alkenyl or alkyl succinimide is from about 0.5:1 to about 5:1.

37. A product prepared by the process defined in claim 36 wherein the molar charge of the cyclic carbonate to the basic nitrogens of the alkenyl of alkyl succinimide is from about 1:1 to 3:1.

38. A product prepared by the process defined in claim 37 wherein the molar charge of the cyclic carbonate to the basic nitrogens of the alkenyl or alkyl succinimide is approximately 2:1.

39. A product prepared by the process which comprises (a) contacting a polyamino alkenyl or alkyl succinimide with a linear polycarbonate at a temperature sufficient to cause reaction wherein the molar ratios of the individual carbonate units of said linear polycarbonate to the basic amine nitrogen of the polyamino alkenyl or alkyl succinimide employed in the process of this invention is from about 0.1 to about 5:1; (b) reacting the product of (a) above with an alkenyl or alkyl succinic anhydride of the formula:

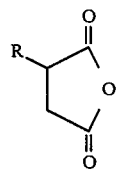

wherein R is alkenyl or alkyl of from 10 to 300 carbon atoms and wherein the process employs from about 0.1 to 1.5 equivalents of the alkenyl or alkyl succinic anhydride per equivalent of the modified polyamino alkenyl or alkyl succinimide of (a) above.

40. A product prepared by the process defined in claim 39 wherein the alkenyl or alkyl group of said polyamino alkenyl or alkyl succinimide contains from 10 to 300 carbon atoms.

41. A product prepared by the process defined in claim 40 wherein said linear polycarbonate is a polycarbonate of the formula:

wherein $R_{15}$ is a hydroxyhydrocarbyl of from 2 to 20 carbon atoms; $R_{16}$ is a divalent hydrocarbyl group of from 2 to 20 carbon atoms; m is an integer of from 1 to 10; and n is an integer of from 1 to 300.

42. A lubricating oil composition comprising an oil of lubricating viscosity and an amount effective to provide dispersancy of a product as defined in any of the claims 1, 2, 3, 4, 6, 8, 9, 10 11, 13, 14, 15, 16, 17, 21, 22, 23, 24, 30, 31, 32, 33, 34, 35 and 39.

43. A lubricating oil concentrate comprising from about 90 to 10 weight percent of an oil of lubricating viscosity and from about 10 to 90 weight percent of a product as defined in any of claims 1, 2, 3, 4, 6, 8, 9, 10, 11, 13, 14, 15, 16, 17, 21, 22, 23, 24, 30, 31, 32, 33, 34, 35 and 39.

* * * * *

UNITED STATES PATENT AND TRADEMARK OFFICE
CERTIFICATE OF CORRECTION

PATENT NO. : 4,840,744
DATED : June 20, 1989
INVENTOR(S) : ROBERT H. WOLLENBERG, ET AL.

It is certified that error appears in the above-identified patent and that said Letters Patent is hereby corrected as shown below:

Claim 3, Col. 39, Line 19, "Claim 1 wherein" should read --Claim 2 wherein--

Claim 13, Col. 40, Line 34, " $(HO)_t$ " should read -- $(HO)_t$ --

Claim 13, Col. 40, Line 44, " $(HO)_t$ " should read -- $(HO)_t$ " --

Claim 22, Col. 42, Line 34, "Claim 20" should read --Claim 21--

Claim 39, Col. 46, Line 12, "0.1" should read --0.1:1--

Signed and Sealed this

Twenty-fourth Day of April, 1990

Attest:

HARRY F. MANBECK, JR.

Attesting Officer        Commissioner of Patents and Trademarks